United States Patent [19]

Simpson et al.

[11] Patent Number: 5,605,839
[45] Date of Patent: Feb. 25, 1997

[54] METHODS AND APPARATUS FOR USE IN SEQUENTIAL CHEMICAL REACTIONS

[75] Inventors: Richard J. Simpson, Richmond; Antony W. Burgess, Camberwell; Robert L. Moritz, Victoria, all of Australia

[73] Assignee: Ludwig Institute for Cancer Research, N.Y.

[21] Appl. No.: 891,162

[22] Filed: May 29, 1992

Related U.S. Application Data

[63] Continuation-in-part of Ser. No. 842,363, filed as PCT/AU91/00141, Apr. 11, 1991..

[30] Foreign Application Priority Data

Apr. 11, 1990 [AU] Australia ................... PJ9605

[51] Int. Cl.$^6$ .................................................. G01N 33/50
[52] U.S. Cl. ........................... 436/89; 436/161; 436/180; 422/50; 422/186.04
[58] Field of Search .................... 436/86–90, 149, 436/150, 151, 161, 173, 175, 177, 178, 180; 422/101, 82.01, 82.02, 186.04, 67, 50; 204/299 R, 302, 180.1, 186

[56] References Cited

U.S. PATENT DOCUMENTS

| | | |
|---|---|---|
| 3,338,812 | 8/1967 | Dworak et al. ................. 204/195 |
| 3,717,436 | 2/1973 | Penhasi et al. . |
| 3,725,010 | 4/1973 | Penhast . |
| 4,065,412 | 12/1977 | Dreyer ............................. 260/8 |
| 4,155,714 | 5/1979 | Bonner et al. . |
| 4,603,114 | 7/1986 | Hood et al. ........................ 436/89 |
| 4,610,847 | 9/1986 | Hood et al. ...................... 422/102 |
| 4,665,037 | 5/1987 | Stolowitz ......................... 436/89 |
| 4,704,256 | 11/1987 | Hood et al. ...................... 422/68 |
| 4,820,648 | 4/1989 | Capridi et al. .................. 436/89 |
| 4,863,870 | 9/1989 | Stolowitz et al. ............... 436/89 |
| 5,057,438 | 10/1991 | Imai et al. ....................... 436/516 |
| 5,151,165 | 9/1992 | Haynh ............................. 204/299 R |

FOREIGN PATENT DOCUMENTS

| | | |
|---|---|---|
| 0395319 | 10/1990 | European Pat. Off. . |
| 1019893 | 5/1962 | United Kingdom . |
| 1229890 | 6/1969 | United Kingdom . |
| 2146550 | 4/1985 | United Kingdom . |

Primary Examiner—Jeffrey R. Snay
Attorney, Agent, or Firm—Felfe & Lynch

[57] ABSTRACT

This invention relates to methods and apparatus for carrying out chemical reactions between a plurality of reactants and in particular it is amenable to micro or nano scale operation and to the sequential chemical reactions required during such processes as construction or sequencing of proteins, oligonucleotides and polysaccharides. The present invention further relates to a capillary liquid chromatography system for high-sensitivity component separation and microsequencing for use in association with the methods and apparatus herein described.

10 Claims, 18 Drawing Sheets

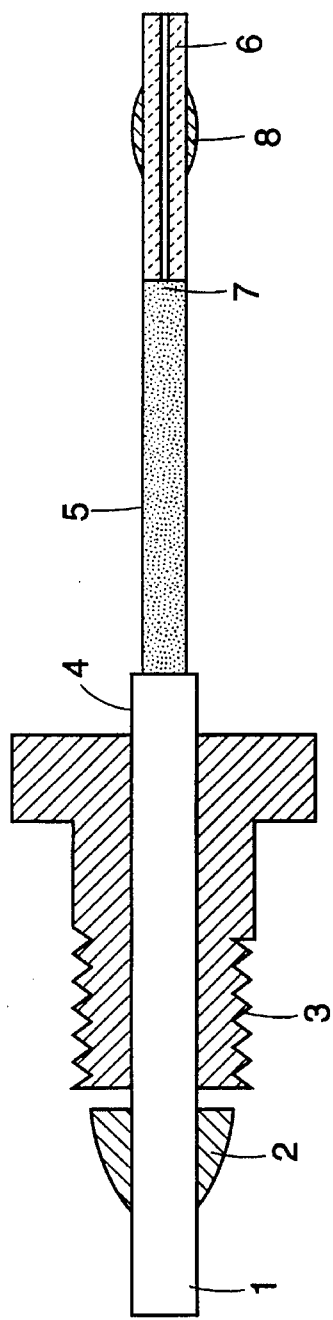
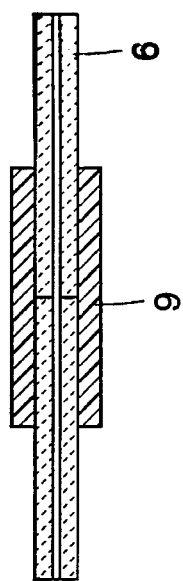
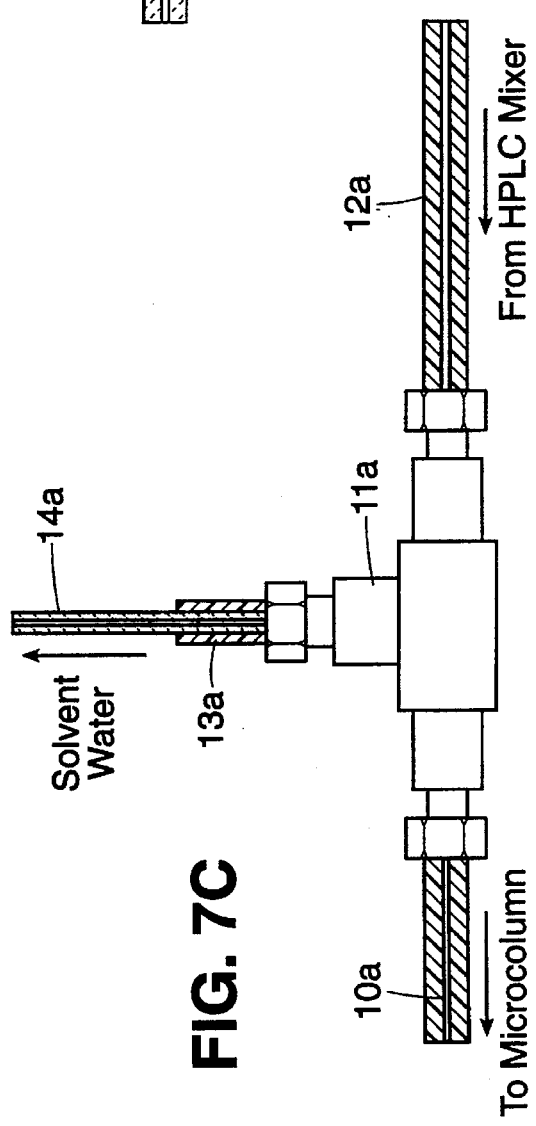
FIG. 7B
FIG. 7D
FIG. 7C

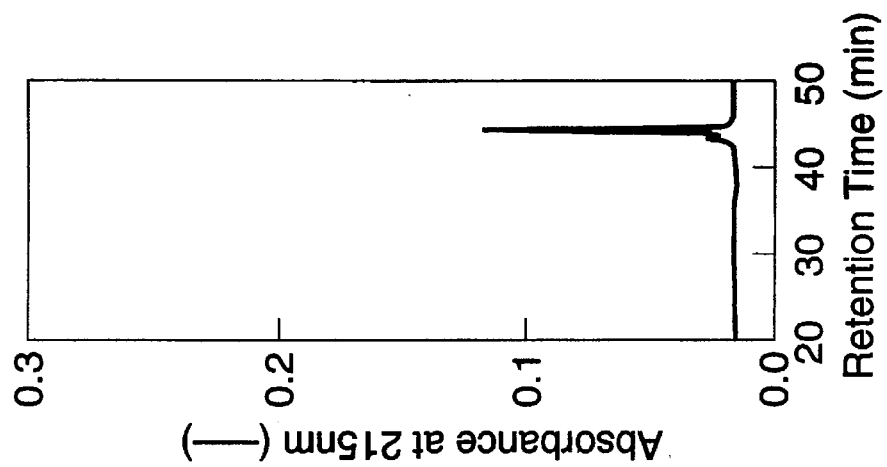
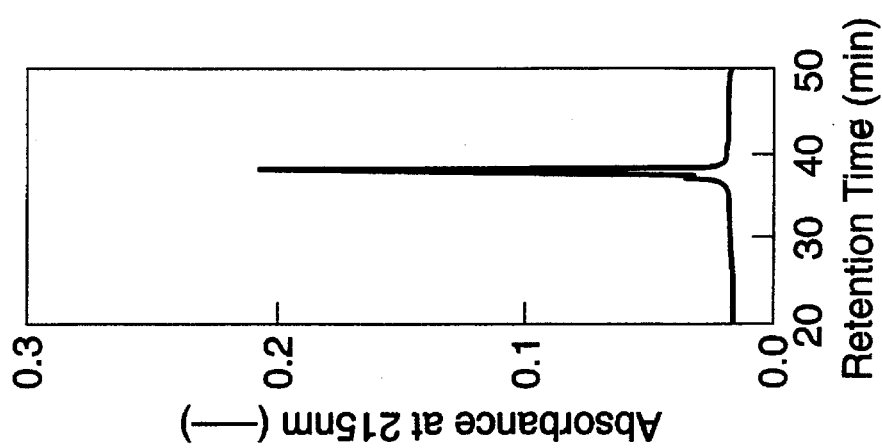
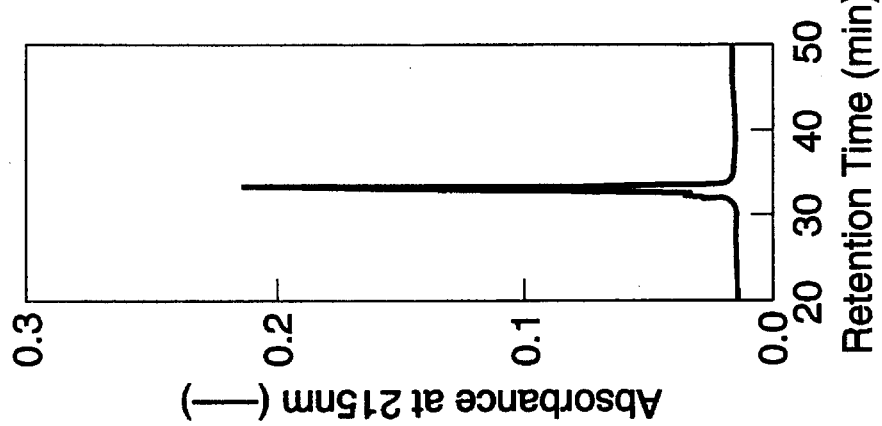

METHODS AND APPARATUS FOR USE IN SEQUENTIAL CHEMICAL REACTIONS

RELATED APPLICATIONS

This is a continuation-in-part of copending application Ser. No. 842,363 filed Mar. 25, 1992, which was based on the International Application No. PCT/AU91/00141, filed on Apr. 11, 1991.

FIELD OF THE INVENTION

This invention relates to methods and apparatus for carrying out chemical reactions between a plurality of reactants and in particular it is amenable to micro or nano scale operation and to the sequential chemical reactions required during such processes as construction or sequencing of proteins, oligonucleotides and polysaccharides. The present invention further relates to a capillary liquid chromatography system for high-sensitivity component separation and microsequencing for use in association with the methods and apparatus herein described.

BACKGROUND TO THE INVENTION

A classic example of a sequential chemical reaction is the Edman protein sequencing technique involving the stepwise removal and identification of the N-terminal amino acid residues of a protein. The traditional Edman technique involves coupling the N-terminal amino acid residue to phenylisothiocyanate (PITC) in a solvent under alkaline or anhydrous conditions to form a phenylthiocarbamyl derivative. Excess PITC (usually at least 100 fold molar excess) is removed, typically by liquid extraction and the solvent also removed. The N-terminal amino acid, coupled to the PITC is subjected to cleavage by anhydrous acid to form an anilinothiazolinone (ATZ) derivative of the amino acid. The ATZ derivative is removed for subsequent chromatographic identification of the amino acid portion. The original protein is thus truncated, at its N-terminal by one amino acid allowing access to the formerly penultimate amino acid to be coupled, cleaved and identified with a subsequent Edman cycle. Further cycles can be undertaken to determine the entire sequence of the protein.

Some of the disadvantages of the traditional liquid phase Edman technique include the necessity to introduce plural incompatible reagents to achieve the coupling and cleavage steps for each cycle. In particular it is noted that strong alkali conditions are required in the coupling step whereas a strong acid environment achieves the cleavage. Clearly differentiation of these strong reagents is required to ensure a consistent removal of all the N-terminal residues without also generating spurious derivatives or uncoupling further non terminal residues. Furthermore the requirement for removal of the various volatile and non volatile auxiliary reagents and solvents during each cycle leads to sample loss and/or the formation of insoluble by-products. Relatively large volumes of sample and reagents are also required.

Effective automation of the Edman technique is first described in Edman and Begg, "A Protein Sequenator", in the European J. Biochem. 1, (1967), 80–91 and in U.S. Pat. No. 3,725,010. In these sequenators a liquid phase Edman technique is carried out in a thin film formed on the inside wall of a rotating reaction cell, now termed a "spinning cup". The spinning cup is located within a closed reaction chamber to maintain an inert atmosphere. Reagents are added to the cup by a system of pumps and valves and material removed by overflow over the lip of the spinning cup, vacuum evaporation or by dissolving or extracting in non polar solvents. The liquid reagents and solvents themselves form films on the walls of the spinning cup which pass over and interact with the sample film as the cup spins. The reagents dissolve the sample film and perform the coupling and cleavage stages of the Edman process, after which volatiles are removed by evacuation and the remaining sample film solvent extracted to transfer resulting amino acid thiazolone for identification.

It will be apparent that this dynamic system, requiring fluid and vacuum seals is difficult to construct and operate. The agitation induced by the spinning cup can cause the sample film to be overly extracted during washing or dislodged, in particular if the small protein being sequenced is a polypeptide. The initial protein sample must therefore be relatively large in volume and chain length. The drying of the protein onto the inner wall of the spinning cup must also be performed very carefully and slowly to achieve an even thin film while avoiding boiling and splatter during desiccation. Precise metering of reagents and solvents into the cup is also required to ensure consistency between cycles.

Laursen, in the European J. Biochem. 20 (1971), and Waschter et al., FEBS LeH 35, 97 (1973), described alternative automatic sequencers in which the sample is immobilized by covalent linkage to the surface of a bead matrix/gel type solid phase. This allows all reagents and solvents to be removed by solvent replacement rather than vacuum evaporation or other drying. Solvent replacement techniques, however, necessitate covalent linkage of the sample to avoid washout by the solvents used. U.S. Pat. Nos. 4,704,256, 1,610,847 and 4,603,114 relate to similar technologies in which the sample is embedded in a permeable matrix and subject to liquid solvents.

Drawbacks of the solvent systems as discussed above have led to gas solid phase Edman techniques, for instance as described in U.S. Pat. Nos. 3,892,531 and 4,065,412. In the former patent the sample is attached to a finger like extension within a reaction chamber, while the latter applies the sample to inner and outer surfaces of macroporous beads. In each system at least one of the reagents is introduced in the gaseous form; however neither system is amenable to contamination free, multiple cycles due to inefficiencies in washing by dew formation on the finger or by channelling of the solvent between rather than through the beads.

Each of the above mentioned sequenators have required undesirably large samples due to various inefficiencies in washing etc. British Application No. GB 2146550 describes an attempt to miniaturize a reaction flask suitable for Edman technique having capillary tubes to spray wash interior walls bearing an immobilizing sample matrix. Fluids within the flask can be agitated by the introduction of a gaseous phase. There is still, however, a need for systems more amenable to miniaturization and using even smaller samples. There is also a need for systems allowing direct interfacing of the chemical reactor with identification or assay apparatus such as mass spectrometers, chromatographs etc.

The above described Edman technique for terminal degradation of a protein, successively removed N-terminal residues. Alternative systems using a C-terminal degradation, such as phosphoryl mercaptobenzothiazole or benzoyl isothiocyanate are described in "Methods in Protein Sequence Analysis" (1991) Jornvall/Höög/-
Gustavsson (Eds) Birkhäuser Verlag, Basel. The latter system embodies a two stage couple/cleave reaction between the cleaving reagent and C-terminal amino acid, rather like the Edman technique. Further guidance on protein sequencing is founding in Schlack et al. (1926) Hoppe-Seylers, Z. Physiol. Chemie., 154, 126–170 and Stark (1972) "Methods in Enzymology", Hirs/Timascheff (Eds) Academic Press, 25, 369.

The above description of previous techniques and apparatus has centered on protein sequencing, but it will be readily apparent that many other chemical processes face similar problems of sample loss or contamination, inefficient or overly vigorous washing, inefficient access of reagents etc. Examples of such reactions include site specific modification, construction or sequencing of other macromolecules.

In work leading up to various aspects of the present invention, the inventors also became involved in the development and application of microbore column liquid chromatographic techniques that are compatible with high-sensitivity microsequencing methodologies.

Compared to their conventional column counterparts (4.6-mm Internal Diameter (I.D.)), microbore columns (1–2.1-mm I.D.) offer enhanced mass sensitivity (5–20-fold) and decreased peak volumes (40–60 µl) without any striking diminution of resolution. Microbore column liquid chromatography is now widely used for peptide mapping with proteases, complete protein structure determinations, isolation of proteins form acrylamide-gel electroeluates and detergent mixtures. More recently, microbore chromatography has been used in tandem with mass spectrometry.

Although there has long been a desire to further miniaturise liquid chromatography, progress has been restricted to the availability of packed capillary columns and instrumentation designed to facilitate the operation of such columns.

SUMMARY OF THE INVENTION

In accordance with a first aspect of the present invention there is provided a method of conducting a chemical reaction, the method comprising immobilizing a first reactant at a reaction locus, electrophoretically introducing to the reaction locus at least one charged additional reactant and after reaction between the first and additional reactants removing the remaining additional reactant and/or a reaction by-product of the reaction from the reaction locus.

A related aspect of the invention provides chemical reaction apparatus comprising a reaction locus, immobilizing means for securing a first a reactant at the reaction locus, means for the electrophoretic introduction to the reaction locus of at least one additional reactant and means to remove, from the locus, the remaining additional reactant and/or a reaction by-product of the first and additional reactants.

A second aspect of the invention provides a method of conducting a chemical reaction, the method comprising immobilizing a first reactant at a reaction locus, introducing an additional reactant to the reaction locus, allowing a reaction between the first and additional reactants to produce a reaction by-product, if the reaction by-product is not charged, imparting an electrical charge to the reaction by-product and electrophoretically removing, from the reaction locus, the by-product for collection or analysis.

A related aspect of the invention provides apparatus for conducting a chemical reaction, the apparatus comprising a reaction locus, immobilizing means for securing a first reactant at the reaction locus, means to introduce an additional reactant to the reaction locus, optionally means to impart a charge to a reaction by-product of a reaction between the first and additional by-products and means to electrophoretically remove from the reaction locus, the reaction by-product.

A third aspect of the invention provides a method of conducting a chemical reaction, the method comprising immobilizing a first reactant at an electrode defining a reaction locus, introducing at least one additional reactant to the reaction locus, electrolytically activating a reaction between the first and additional reactants by energizing the electrode and thereafter removing from the reaction locus, remaining additional reactant and/or a reaction by-product of the reaction.

A fourth aspect of the present invention contemplates the resolution, separation and/or purification of one or more components in a sample comprising passing said sample through a capillary liquid chromatographic system, said system comprising a capillary column packed with bonded-phase particles for a time and under conditions sufficient to resolve, separate and/or purify the components. Preferably the chromatographic system is as herein described and the component is a protein, polypeptide, peptide PTH-amino acid or derivatives thereof. Preferably the sample is passaged at a flow rate of from 1–20 µl/min., more preferably 2–10 µl/min. and most preferably 2–5 µl/min. Using this system, proteins are recoverable in volumes of from about 1 to about 20 µl and preferably from about 2 to about 8 µl.

A fifth aspect of the present invention provides a method for conducting a chemical reaction using one or more reactants resolved, separated and/or purified using a capillary liquid chromatographic system as herein described, said method comprising immobilizing a first reactant at an electrode defining a reaction locus; introducing an additional reactant to the reaction locus; electrolytically activating a reaction between the first and additional reactants; and removing remaining additional reactant and/or a reaction by-product from the reaction locus. Preferably, the additional reactant is an electric charge and the electrode is energised to electrophoretically introduce the additional reactant in the reaction locus and to cause the electrolytic activation.

A sixth aspect of the present invention contemplates an assembly or apparatus for the resolution, separation and/or purification of components such as proteins, polypeptides, peptides, amino acids and the like comprising a capillary liquid chromatographic system as hereinbefore described, the apparatus or assembly further having associated therewith an electrode disposed at a reaction locus; means to immobilize a first reactant at the reaction locus; means to introduce an additional reactant to the reaction locus; means to energize the electrode to thereby electrolytically activate a reaction between the first and additional reactants and/or to electrophoretically attract the additional reactant to the reaction locus; and means to remove from the reaction locus, remaining additional reactant and/or a reaction by-product of the reaction.

A seventh aspect of the invention provides a method of conducting a chemical reaction, the method comprising immobilizing a first reactant at a reaction locus, introducing an additional reactant to the reaction locus, allowing a reaction between the first and additional reactants to produce a reaction by-product, if the reaction by-product is not charged, imparting an electrical charge to the reaction by-product and electrophoretically removing, from the reaction locus, the by-product for collection or analysis wherein one or more of the reactants and/or products is separated, purified or otherwise resolved by capillary liquid chromatography as herein described.

An eighth aspect of the invention provides apparatus for conducting a chemical reaction, the apparatus comprising a reaction locus, immobilizing means for securing a first reactant at the reaction locus, means to introduce an additional reactant to the reaction locus, optionally means to impart a charge to a reaction by-product of a reaction between the first and additional by-products and means to electrophoretically remove from the reaction locus, the reaction by-product and said apparatus further comprising means for capillary liquid chromatography to separate, purify or otherwise resolve one or more of the reactants and/or products.

The methods and apparatus defined above may be particularly suited to sequential chemical reactions between the first reactant and a plurality of individual second and subsequent reactants when one or more of such reactants and/or any products therefrom are separated, purified or otherwise resolved by capillary liquid chromatography.

BRIEF DESCRIPTION OF THE FIGURES

FIGS. 7A–7D are a schematic diagram of the gradient capillary HPLC used in accordance with the present invention.

FIG. 8 is a graphical representation showing the effect of column internal diameter and flow rate in detector sensitivity.

DETAILED DESCRIPTION OF THE INVENTION

Figure 1:
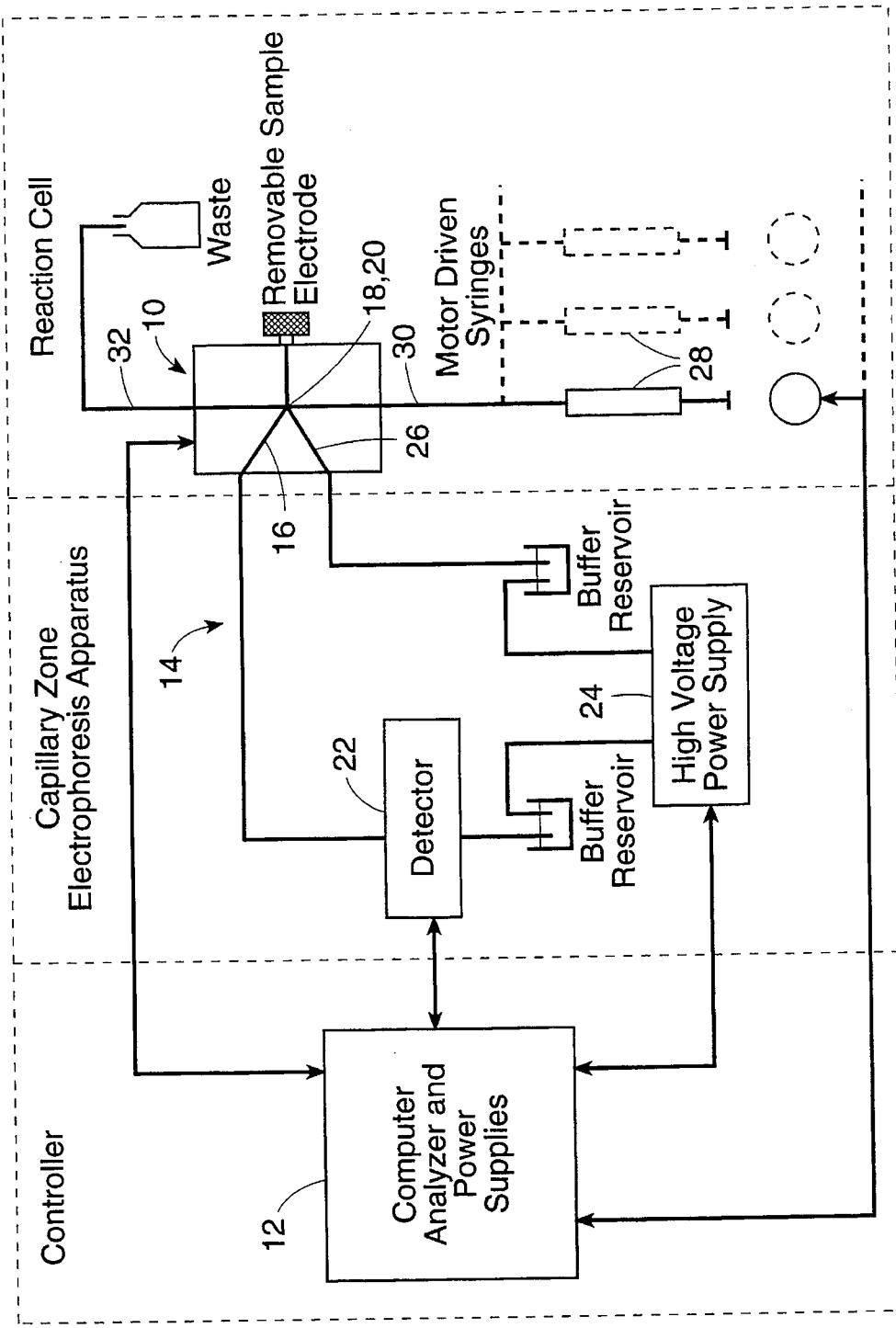
FIG. 1 is a schematic plan of a first embodiment of the reaction apparatus in conjunction with ancillary analysis and control equipment.

By the use of the present invention the electrophoretic introduction of the additional reactant causes it to focus or concentrate around the electrode upon which is immobilized the first reagent. Thus a relatively dilute concentration of the additional reactant can achieve enhanced concentrations and therefore reaction efficiencies. Comparatively weak feed solutions of the additional reactant have the advantage of facilitating washing out thereof prior to subsequent reactant additions, thereby minimizing contaminating carry-over.

In the context of this specification "chemical reactions" is being used in its classical sense denoting a molecular level interaction between the first and additional reactants resulting in a chance in structure of one or both reactants and includes such interactions as enzymatic reactions. Furthermore, "electrophoretic" includes "electrokinetic".

The first reactant will typically be immobilized immediately adjacent an electrode serving to cause electrophoretic migration of the charged additional reactant. Preferably the first reactant is immobilized on such an electrode itself or on a sample matrix extension thereof.

At its simplest, the above mentioned means to remove remaining additional reactant and/or reactant by-product flush these materials away from the reaction locus. Suitably controlled syringes or pumps can be used to achieve this. The method and apparatus of this aspect of the invention may however be adapted to the collection and/or identification of a reaction by-product of the first and an additional reactant. A convenient arrangement where the by-product is itself charged or can be made charged provides electrophoretic or electrokinetic means to selectively remove the by-product for subsequent analysis away from the reaction locus by, for instance, mass spectrometry or capillary electrophoresis. These analytical techniques use extremely small samples. As the apparatus and method of the invention are amenable to micro and nano scale reactions, direct injection of the by-product described above into the sample port of the analysis instrument becomes possible thus minimizing losses and inaccuracies which may occur, for instance, during sample dilution in prior art methods. Other appropriate analysis equipment may involve electromagnetic absorption, fluorescence, nuclear resonance, immunological detection, gas liquid chromatography GLC etc.

The above mentioned arrangement having electrophoretic removal of reaction by-products is not necessarily limited to a set-up in which the additional reactant(s) is/are introduced electrophoretically.

Conveniently an ion exchange membrane intermediate the reaction locus and the injection port is used to separate the by-product from other species in the reaction portion of the apparatus. Ion exchange membranes such as BIO-REX products having AG ion exchange resin beads permanently enmeshed in a polyfluoroethylene matrix are available with a number of ion exchange varieties suitable for separating different species of by-products, both cationic and anionic.

Where a reaction by-product is directly injected into the sample port of an analysis apparatus, electrophoretically or otherwise, it is desirable to employ a phase contrast between the reaction locus medium and the analysis medium. For instance where the medium around the reaction locus comprises a non polar medium, a polar medium in the sample injection port of the analysis apparatus in conjunction with a suitable hydrophobic membrane can assist in separating the by-product from the reaction solvent or diluent. An example can be taken from the above noted Edman technique which utilises an organic medium. In contrast a capillary electrophoresis analyser can run on an aqueous medium. Separation of the by-product is efficiently achieved through a hydrophobic reaction locus medium by a porous hydrophobic membrane composed of polytetrafluoroethylene. Conversely in other reaction systems an aqueous reaction medium around the reaction locus may encourage the use of non polar chromatographic detection techniques in conjunction with porous hydrophilic membranes.

The methods and apparatus defined above may be particularly suited to sequential chemical reactions between the first reactant and a plurality of individual second and subsequent reactants. Thus a first reaction may be commenced by electrophoretically introducing a second reactant to the first reactant following which unreacted second reactant and reaction by-products can be flushed away or electrophoretically removed. Thereafter a third reactant may be (electrophoretically) introduced to the reaction locus for reaction with an immobilized reaction product of the first and second reactants. In this way an ordered sequence of reaction products, as may be used in the construction of macromolecules such as polysaccharides, oligonucleotides or proteins may be built up on the immobilized first reactant. It will of course be necessary to provide such additional reactant "building blocks" with a suitable charge to ensure their electrophoretic migration to the "foundation" first reactant. It will also be necessary, if a macromolecule having an ordered sequence is to be built up, to ensure that the additional reactant bonds at the desired terminal of the incipient macromolecule. To this end appropriate capping enzymes (such as glycosyl transferases for polysaccharides or ribosomal transferases for proteins) can be introduced into the reaction medium. Alternatively acid or base catalysed condensations can be enhanced by in situ acid/base generation as described later.

Alternative sequential chemical reactions occur in protein, oligonucleotide or polysaccharide sequencing. The prior art discussion above in relation to the Edman technique or C-terminal degradation of a protein is an example of such sequencing reactions. When the present invention is applied to such sequencing reactions, the first reactant can comprise the protein, oligonucleotide or polysaccharide to be sequenced, while the additional reactant may comprise a cleaving agent, successive aliquots of which can be introduced to the macromolecule first reactant. The cleaved off by-product i.e. amino acid, nucleic acid or saccharide, can be collected for analysis after the reaction of the macromolecule with each aliquot of cleaving agent and before the next aliquot of cleaving agent is introduced to the immobilized macromolecule. By appropriate choice of charge for the respective reactants and by-products, the additional reactant and/or by-product of the reaction can be electrophoretically separated for subsequent analysis of the by-product and/or collection of unreacted additional reactant for reuse or discard.

Furthermore, if unreacted additional reactant is electrophoretically removed from the reaction locus and collected at a collection locus adjacent a collection electrode it is possible, by reversing the respective voltages of collection and reaction locus electrodes, to cause a second aliquot of the additional reactant for instance a cleaving reagent in a sequencing system to be reintroduced to the reaction locus from the collection locus. The collection locus thus operates as a reservoir for the additional reactant.

Alternative reactions involving macromolecules and amenable to the present invention include the immobilizing of an enzyme such as a restriction endonuclease or endopeptidase to allow analysis of the nucleotide or polypeptide structure not requiring end terminal truncation. Conversely a peptide or nucleic acid of interest could be immobilized and subsequently introduced to a series of peptidase or nucleases to determine cleavage pattern. Such as approach is useful in determining, e.g. if fusion proteins have been produced by a recombinant host or in DNA restriction analysis.

It is also contemplated that the structure of macromolecules other than proteins, polysaccharides and nucleotides such as long chain lipids, glycoproteins and glycolipids could be determined using techniques of the invention, typically utilizing enzymic cleavage.

A useful feature forming a third aspect of the invention but also observed in the above described electrophoretic apparatus and methods is that energizing of an electrode having the first reactant attached thereto can electroactivate reagents in the medium nearby. For instance a negatively charge electrode will attract positively charged reactants. Additionally it can electrolyse, to some extent, reagents or solvents nearby or in some circumstances the first reactant. Such electrolysis can assist in activation of certain reactions or provide acid or base conditions immediately adjacent the electrode. For instance in the earlier discussed classic Edman technique, a base environment is required to react the Edman reagent i.e. the isothiocyanate coupling agent to the N-terminal amino acid. Traditionally the base conditions are provided by adding a strong base such as Quadrol (Wyandotte Chemicals Corp.) buffer to the reaction vessel. It has now been discovered, however, that basic conditions can be generated in situ adjacent the sample by electrolysis following energizing of the electrode bearing the first reagent. Similarly acid conditions required, for instance, in the cleavage step of Edman procedures can be generated in situ by positive charge energizing of the electrode. It should be noted that this aspect of the invention is not limited to electrophoretically transferred reagents as non charged Edman reagents such as PITC can also be "electroactivated" by basic conditions produced by a negatively charged electrode.

Further provided by this invention and related to this third aspect, is chemical reaction apparatus comprising an electrode defining a reaction locus, means to immobilize a first reactant at the reaction locus, means to introduce an additional reactant to the reaction locus, means to energize the electrode thereby electrolytically activating a reaction between the first and additional reactants and means to remove from the reaction locus remaining additional reactant and/or a reaction by-product of the reaction.

With this aspect of the invention, the electroactivation of the reaction between first and additional reactants can either be by in situ generation of appropriate pH conditions to enhance reaction kinetics (as with the Edman technique example described immediately above). It will also be apparent that in alternative reaction systems active radicals can be formed in situ, adjacent the electrodes by direct electrolysis of the first or more usually the additional reactant.

Electrolysis to product electroactivated species will occur most efficiently where the field strength is strongest. It is thus desirable to immobilize the first reactant immediately adjacent a conductor such as a platinum, such that the electric field strength through the first reactant is maximized. In effect a sample matrix immobilizing the first reactant becomes an extension of the electrode itself.

Referring still to the "electroactivating" aspect of the invention, as with the earlier described first aspect of the invention, the means to remove the remaining additional reactant and/or reaction by-product may simply comprise a pump or syringe to flush the reaction locus. Preferably however, the method and apparatus allow the collection and/or identification of a reaction by-product. As described above electrophoretic means can be provided to selectively remove the by-product, if it is charged, for subsequent analysis away from the reaction locus. Where a by-product does not inherently bear a charge, introduction of charged surfactants, such as SDS sodium dodecyl sulphate can render such materials electrophoretically migratable.

It will be apparent that each of the above described aspects of the invention are amenable to micro and nano scale construction and operation. Reaction locus volumes of less than $1\times10^6$ nl, preferably $1\times10^3$ nl and even of the order of 10 nl to 100 nl are achievable and desirable. Correspondingly small ampages of electrolytic or electrophoretic current, of the order of fractions of a milliamp—for instance 0.01 to 10 µA can be used. Low currents assist in preventing temperature surges in the cell. This has many advantages over current more macro scale techniques in macromolecular construction and sequencing. It allows the use of extremely small amounts of the reactant immobilized at the reaction locus. This is particularly important in sequencing work where the nucleotide, protein or polysaccharide may not be available in large quantities or, as has been discovered during the use of prior art techniques discussed above, may be difficult to manipulate in small quantities. As mentioned above a micro or nano scale operation allows direct injection of reaction by-products (i.e. cleavage residues) into highly sensitive analysis apparatus without requiring dilution or other preparation steps.

Referring still to the advantages of micro or nano scale operation, difficulties in effectively washing the reaction locus without disturbing the immobilized reagent, a particular problem in many prior art techniques, is lessened in the present invention where comparatively small amounts of reagents, diluents and washes can be used. In this regard it will be recalled that in the electrophoretic aspect of the invention, comparative weak reagent concentrations, can be tolerated due to the electrophoretic focussing of the active reagent at the reaction site. Weakly concentrated reagents are of course more easily removed and washed away than more concentrated solutions known in the prior art. Additionally, or alternatively, in the electrolytic aspect of the invention, electroactivation in situ of reagents can allow the use of less concentrated reagent feedstock, and/or eliminate the need to add strong pH control agents. Again the effect of this is to facilitate removal of unwanted reagents and by-products thus preventing carry-over and contamination of subsequent reactions at the reaction locus.

With any of the above defined aspects of the invention, immobilization of the first reactant, typically on all electrode is required. Several of the prior art techniques discussed above have immobilized proteins via covalent linkages. Securing the reagent strongly was important to prevent loss of the sample during the various reactions and washings but is difficult to achieve without adversely affecting the reagent. In contrast the present invention allows gentler methods of attachment of the first reagent at the reaction locus. Desirably the first reagent can be adsorbed directly onto a porous matrix which allows access of the additional reagents to the first reactant particularly its end terminals. Many such matrices are known for polysaccharides, proteins and nucleotides. Examples of such matrices include PVDF, nitrocellulose, glass, quartz, activated glass, activated quartz, cellulose, derivatized cellulose, nylon, plastic or activated plastic. Adsorption in this fashion, unlike covalent binding assists in preserving the structure of the first reagent which is particularly important in sequencing and macromolecule construction operations.

Reaction kinetics will, of course, differ between different combinations of reactants. In the case of a sequential chemical reaction, such as terminal degradation sequencing each residue along the chain may have differing kinetics of reaction with a cleavage reagent. Proline, for instance, in Edman degradation techniques requires a longer reaction time to achieve complete coupling than other amino acids. It is thus desirable to be able to monitor extent of reaction within the cell. This can be achieved colorimetrically by utilizing redox indicators which change colour or absorbance as the redox potential at the reaction locus changes. Other spectrophotometric techniques including laser induced fluorescence are also available which have the advantage of not requiring additional reagents at the reaction locus. Alternatively the extent of reaction can be measured amperometrically by monitoring current through an electrode defining the reaction locus. Thus a plateauing of electrolytic activation can be used to indicate completion of a coupling or cleavage reagent.

The present invention also provides a capillary liquid chromatographic system permitting inter alia gradient elution from reverse-phase capillary (e.g. 0.32 mm I.D.) colums and thus allowing high-sensitivity component (e.g. protein) separation and amino acid microsequencing.

Advantageously, the capillary liquid chromatographic system can be evaluated in terms of its ability to resolve mixtures of proteins, peptides or phenylthiohydantoin(PTH)-amino acid derivatives although the present invention extends to the separation, resolution and/or purification of all suitable biological components or their derivatives. In a most preferred embodiment, the capillary liquid chromatographic system permits minimal detectable amounts for proteins of 40–200 picograms, more preferably 50–100 picograms and most preferably 50–60 picograms. When the column is evaluated using PTH-amino acids, the minimal detectable amount is 20–200 femtomoles, preferably 25–100 femtomoles and most preferably 25–35 femtomoles.

In a most advantageous embodiment, the sample is a gradient eluent from a microbore liquid chromatograph split ahead of an injector so that an accurate percentage (1–5%, preferably 2–3%) of the mobile phase is delivered by pump flows through the capillary column. Furthermore, for convenience, the outlet of the capillary column is connected to a length of fused-silica capillary tubing, preferably 0.075 mm I.D., which is in turn connected to an approximately 6 mm optical pathlength longitudinal capillary flow cell although other detection systems can be employed without departing from the scope of the present invention.

Although the present invention is exemplified by the resolution, separation and/or purification of proteins, peptides or PTH-amino acids, the invention extends to all biological materials including lipids, carbohydrates and nucleic acids and all naturally occurring and synthetic derivatives thereof. Clearly some modification may need to be made to the columns or the separation particles to accommodate the component or sample to be separated but such modifications are encompassed by the present invention.

The present invention is particularly applicable for use in association or complementary with an apparatus for carrying out sequential chemical reactions as hereinbefore disclosed.

Preferably, the first reactant is a macromolecule, the reaction is a cleavage reaction to form the reaction by product, and the reaction by-product and/or the remaining portion of the first reactant is removed for analysis to determine the structure of at least a portion of the macromolecule. Preferably, the analysis comprises capillary electrophoresis on mass spectrometry.

In an alternative embodiment, the analysis is accomplished by capillary liquid chromatography as hereinbefore described whether or not such chromatography is used to first purify the one or more reactants.

In yet another embodiment, the capillary liquid chromatographic system or the apparatus or assembly comprising same together with the chemical reaction means are packaged for sale and optionally in kit form.

Various embodiments of apparatus and methods in accordance with aspects of the invention will now be described by way of example only with reference to the following Examples.

These embodiments of apparatus and methods will be described with reference to protein sequencing by the Edman sequential degradation process. In short, this application of the invention involves immobilizing a protein sample on an electrode at a reaction locus, for instance, within a glass electrophoresis chamber. A first aliquot of a cleaving agent is caused to electrophoretically migrate to the reaction locus to cleave an end amino acid from the immobilized protein. The cleaved amino acid molecules are then electrophoretically transferred to an analysis apparatus, in this case high performance capillary electrophoresis apparatus for identification thereof. Subsequently, second and further aliquots of the cleaving agent can be electrophoretically introduced to the reaction locus to sequentially cleave the remaining amino acids and thus allow the sequence to be determined. The achievement of this method will be discussed in further detail below.

Referring initially to FIG. 1, the reaction apparatus 10 is depicted in conjunction with ancillary computer control device 12 and amino acid analysis apparatus 14 in the form of a capillary zone electrophoresis (HPCE) apparatus of known construction (see for instance Gordon, M. I. et al. (1988) "Capillary Electrophoresis Science", (242):242–248).

In short, the HPCE performs electrophoresis of very small quantities (5–50 nL) within capillary tubing typically of $\leq 100$ μm i.d. In the schematically depicted apparatus 14, the electrophoretic separation column 16 has its sample injection port 18 opening directly into a reaction chamber 20 of the reaction apparatus 10. This arrangement is described in detail below with reference to FIG. 2. The remaining major functions of the HPCE are a detector 22 monitoring the separated species from the column 16, and a high voltage source 24 in communication with the injection port 18 and column 16 through buffer line 26.

The reaction apparatus 10, in addition to the above mentioned reaction chamber 20 includes a plurality of cleavage reactant and flushing agent syringes 28 leading into the chamber 20 via inflow line 30. Leading from the chamber 20 is outflow 32 to waste.

A plurality of electrodes (not depicted in FIG. 1) each with a respective lead, are disposed within the reaction chamber. Each electrode is independently under the control of the computer 12, as are the syringes 28 enabling the method of the invention to be automated. The computer 12 further receives data from the detector 22 of the HPCE 14.

Figure 2:
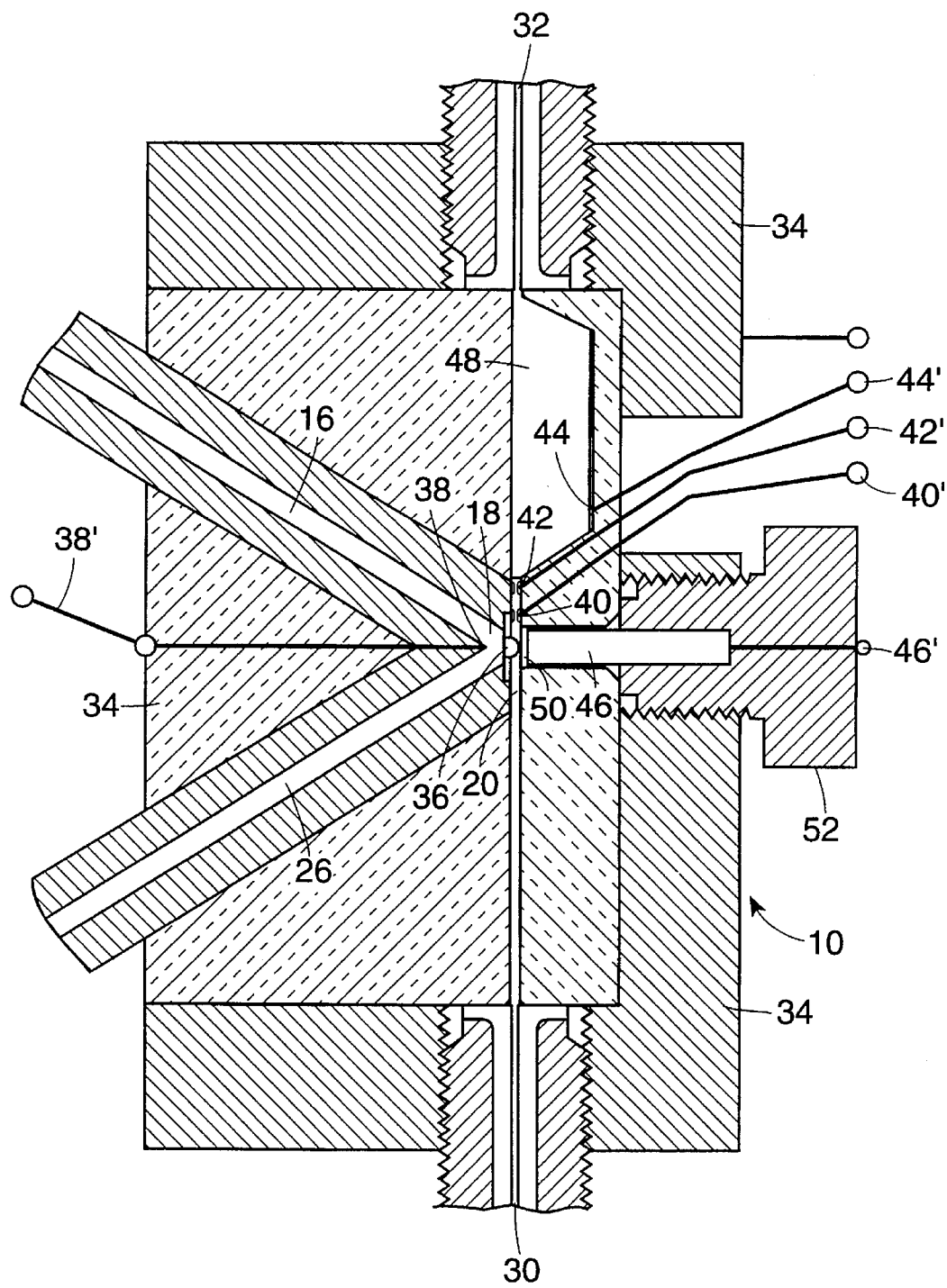
FIG. 2 is a sectional side view of the reaction apparatus of FIG. 1.

Turning now to FIG. 2, the reaction apparatus 10 comprises the electrophoretic reaction chamber 20 defined between a plurality of closely fitted and secured glass blocks 34. Clearly, other inert materials such as glass, quartz, ceramic, plastics etc. may be employed for the construction of a suitable chamber within which to conduct the electrophoretic transfers required by the invention. Conveniently, at least a portion of the material defining the chamber is transparent to allow the use of optical monitoring equipment such as an absorbance spectrophotometer to gauge the progress of reactions at the reaction locus and/or monitor the transfer of reactants or by-products to or from the locus. Advantageously, the material defining the chamber allows the temperature of the contents of the chamber to be kept steady. This may be achieved by an active heat transfer system such as a peltier device.

As mentioned above, leading into the reaction chamber 20, but separated therefrom by a hydrophobic porous PTFE membrane 36 is the sample injection port 18, buffer line 26 and capillary column 16 of the HPCE. An electrode 38 is mounted within the injection port. For simplicity, the electric lead 38' connecting the electrode 38 to the voltage source/ computer 12 has been truncated.

Three further electrodes, 40, 42 and 44 are disposed on an interior wall of the reaction chamber 20 successively downstream of a sample electrode 46 disposed facing the membrane 36 over the HPCE injection port. Each of the electrodes 40, 42, 44 and 46 has a respective lead 40', 42', 44' or 46' which have also been truncated for clarity but lead to the computer 12 for adjustment of respective voltages applied between the various electrodes. Electrode 44, most remote from the sample electrode 46 is disposed on an interior wall portion of an expanded portion 48 of the reaction chamber defining an electrophoretic storage locus as described further below.

When fitted, the sample electrode 46 terminates, within the reaction chamber, at a chemically inert protein immobilizing matrix 50 such as a polyvinylidene difluoride porous membrane. The sample electrode 46 further comprises a removable threaded support 52 to disengageably secure the electrode through the chamber walls. The sample electrode in this embodiment is platinum but other electrically conductive materials such as gold, tungsten or graphite may also be appropriate.

The apparatus is adapted to miniaturization enabling fine temperature and environmental control thereby to optimize the sequential degradation process. The reaction chamber may be, for instance, of the order of a millimetre or significantly less across allowing the use of very low (μA) currents for the electrophoretic transfers. This further assists in preventing temperature surges which may effect the chemical reaction.

Sample loading

In use, the sample (for example, protein or oligopeptide) is immobilized by application, external to the apparatus, to the chemically inert immobilizing matrix (e.g. porous polyvinylidene difluoride (PVDF) membrane 50) affixed to the end of the removable, insulated (PTFE) platinum electrode 46 either by passive means (e.g. direct spotting) or electrotransfer. After sample immobilization, sample electrode 46 is re-installed into the glass blocks defining the reaction chamber so that the end of electrode 46 with the membrane 50 and the immobilized sample is positioned on the internal surface of the electrophoretic reaction chamber 20.

The remainder of the sequencing operation is cyclic and includes the following steps:

1. Initial reaction

Isothiocyanate coupling of immobilized protein or peptide amino groups is achieved by electrotransfer of a positively-charged isothiocyanate (e.g. rhodamine B) dissolved in an anhydrous organic solvent (e.g. 10% n-propanol/90% butyl chloride); to the negative sample electrode 46, the basic conditions required for efficient coupling of isothiocyanates to non-protonated amine groups on the proteins or peptides immobilized at electrode 46 are achieved by the use of an organic solvent soluble acid-base salt (e.g. triethylammonium trifluoroacetate) wherein decomposition to a basic component occurs at the negative sample electrode. The positive electrode in this electrical field (Field 1) is electrode 44. Electrophoretic migration of the pigmented and fluorescent rhodamine ITC can be monitored visually through the transparent glass walls of the cells as can focussing and concentration of the reagent adjacent the electrode 46.

2. Removal of excess reagent

After coupling, unreacted rhodamine B isothiocyanate and its by-products (e.g. thioureas) are electro-phoretically transferred to the storage locus 48 at the expanded portion of the reaction chamber using electrode 44 by reversing the polarity of electrodes 46 and 44 (i.e. electrode 46 is now positive with respect to electrode 44).

As in all Edman degradation techniques it is important to achieve a 100% cleavage of each terminal amino acid residue in each cycle. If this is not achieved, the next cycle of coupling and cleavage may be contaminated with terminal amino acids left uncleaved from the previous cycle. In the illustrated embodiment employing HPCE detection of cleaved residues, extremely small numbers of residues are adequate to achieve an unambiguous identification. Accordingly a relatively small coupling efficiency of the charged ITC reagent can be tolerated. If such a low efficiency coupling reagent is used, it is advisable to introduce a high efficiency Edman reagent after coupling of the electrophoretic moiety to couple to and fill any remaining N-terminal residues thereby to ensure 100% cleavage. Accordingly it is desirable to flush the reaction cell with a phenyl-ITC (PITC) reagent of high coupling efficiency after coupling of the rhodamine ITC. As PITC does not bear an electric charge it cannot be electrophoresed and thus is injected by syringe. Removal of unreacted PITC requires flushing of the cell. It is desirable to accomplish this prior to cleavage of reacted ITC derivatives to ensure that penultimate N-terminal residues are not prematurely coupled by PITC although the basic conditions required for such coupling will generally quickly dissipate when electrolysis around the electrode is ceased.

3. Cleavage step

Concomitant with the polarity reversal of electrodes 46 and 44, decomposition occurs at the positively charged sample electrode 46 as cleavage of the rhodamine B thiocarbamyl amino acid from the immobilized protein or peptide commences. Since this cleavage reaction is relatively slow compared to the electrophoretic movement of unreacted rhodamine B isothiocyanate and its by-products (e.g. thiourea), these latter species will pass electrode 40 before the cleavage reaction has proceeded to any appreciable extent.

4. Transfer of isothiocyanate derivative

Electrode 40 is now made positive with respect to electrode 44, creating an electric field (Field 2) and the electrophoretic migration of the rhodamine B isothiocyanate products continues towards electrode 44. When these products pass electrode 42, this electrode is made positive with respect to electrode 44 (but not as positive as electrode 40) to create an electric field (Field 3) which entraps rhodamine B isothiocyanate near electrode 44 whilst the sample electrode 46 is totally isolated, electrically, from electrodes 44, 42 and 40. At this stage the polarity of electrode 46 is made positive with respect to electrode 38 situated in the injection port 18 of the "capillary electrophoresis" component of the apparatus. The electric field (Field 4) created allows further accumulation of acid and cleavage to occur at the sample electrode 46; the cleaved thiazolinone amino acid derivative (positively charged) migrate through the porous membrane 36 towards electrode 38 in the HPCE sample injection port 18. Separation of the capillary electrophoresis aqueous buffer within the capillary from the anhydrous organic solvent in the reaction chamber is achieved by the hydrophobic membrane 36.

5. Identification of thiazolinone amino acid derivatives

After the completion of the cleavage reaction, the thiazolinone amino acid derivatives which have now accumulated at electrode 38 are identified and quantified with the "capillary electrophoresis" system (for this purpose, electrode 38 is isolated). To further enhance selectivity and sensitivity of detection, the high separation efficiencies of capillary zone electrophoresis can be combined with sensitive fluorescence or mass spectrometric detection (for details said Smith, R.D. et al. (1988) "Capillary Zone Electrophoresis—Mass Spectrometry", Anal. Chem. 60:436–441).

6. Subsequent cleavage cycles

The above-mentioned cycle of the Edman degradation procedure comprising steps 1–5 can be repeated by making the polarity of sample electrode, 46, negative with respect to electrode 44. Alternatively, the regents and solvent in electrophoretic reaction chamber may be replenished during or at the end of each cycle via the syringes 28. If required, additional reagents for coupling, cleavage or flushing solvents may be introduced into the chamber 20 by the use of one or more of the syringes 28 connected to the input 30.

In the above described embodiment, the positively charged rhodamine derivative of ITC was used and this moiety therefore electrophoretically migrated to the reaction locus. The use of such a positively charged reagent is particularly advantageous in a system such as Edman degradation where the coupling reaction requires basic conditions as in situ generation of the base was also occurring at the reaction locus as an auxiliary salt within the medium, triethylammonium trifluoracetate was being electrolysed.

In an alternative acid catalysed system, a negatively charged group such as fluorescein could be attached to a cleavage reagent and electrophoretically attracted towards a positively charged electrode. At the positive electrode electrolysis of an auxiliary reagent or the medium itself could, simultaneously, be creating acid conditions adjacent the first reagent. Clearly where the reaction between first and additional reagents does not required a pH shift, the medium and any auxiliary reagents would be selected to ensure minimal electrolytic action adjacent the electrode. Use of a fluorescent charged group is convenient as it allows easy optical monitoring of reactant transfer and can also assist in combined fluorescent/CE determinations.

Figure 3:
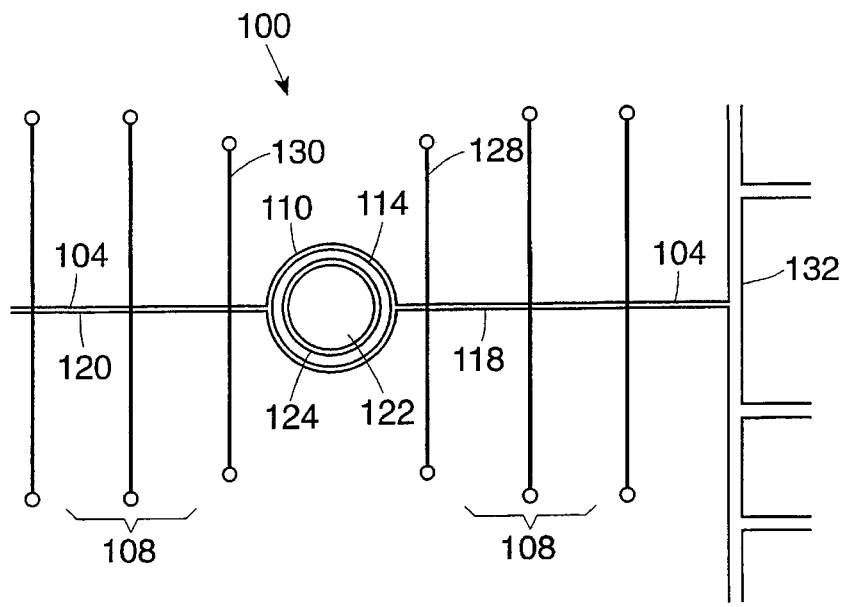
FIG. 3 is a schematic plan view of a second embodiment of reaction apparatus in accordance with the invention.
Figure 4:
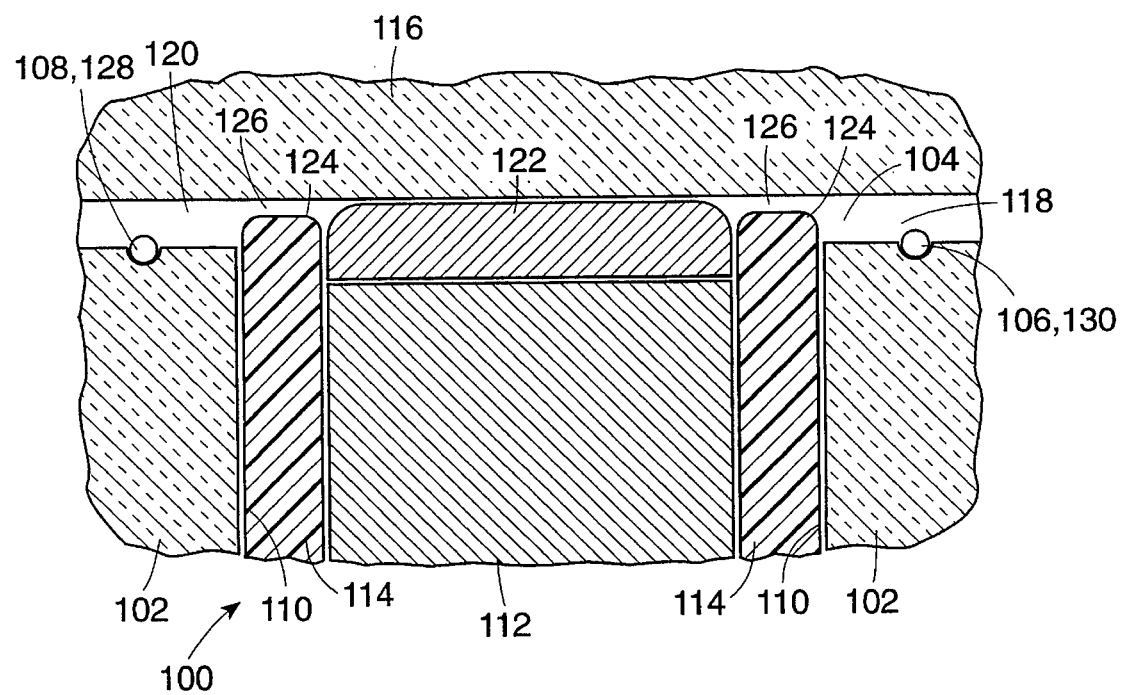
FIG. 4 is a partial sectional side view of the embodiment of FIG. 3.

Referring now to FIGS. 3 and 4 an alternative but generally similar microcell is depicted. In this embodiment the microcell 100, of milled borosilica glass comprises a lower portion 102 having etched therein a longitudinal groove 104 intersected by upstream 106 and downstream 108 sets of three parallel transverse grooves. Bored through the lower portion 102 intermediate the sets 106, 108 of grooves is a vertically extending recess 110 into which is screwed, in use, a 0.8 mm diameter noble metal sample electrode 112 as best seen in FIG. 4. Extending around the electrode is an insulating sheath 114 of PTFE. Sealingly extending over the lower portion 102 is a glass upper portion 116 defining the roof of recess 110 and grooves 104, 106 and 108. The glass upper portion allows direct microscopic observation of the interior of the apparatus and hence allows colorimetric indication of the transfer of reactants. The glass upper cover is omitted in FIG. 3.

In this embodiment recess 110 defines the reaction chamber. Longitudinal groove 104 extending into the chamber defines 0.09 mm diameter upstream 118 and downstream 120 conduit for reagent entry and removal. Extending along each of the transverse grooves in direct electrical communication with the adjacent intersecting conduit 118 or 120 is a respective gold electrode (0.08 mm).

Referring now to FIG. 4, it can be seen that a 0.15 mm deep sample matrix 122 overlies the sample electrode 112. The insulating sheath 114 extends upwardly at reference numeral 124 around the sample matrix although a gap 126 between the sheath and the glass top portion 116 allows entry and exit of reactants from the conduits to the sample matrix. In the described arrangement, the sample matrix 122 of PVDF which except for the insulating sheath, fills recess 110 has a nominal volume 75 nl but with an 80% void volume. The effective reaction chamber in this embodiment is thus 60 nl plus respective volumes of about 1 nl on either side between the recess 110 and the nearest electrode upstream and downstream (respectively 128, 130).

Not depicted in FIGS. 3 and 4 are the downstream analytical device, upstream reagent injection apparatus at manifold 128—Kloehn model 50100 syringe drives, 100 μl syringes, electrical connections between electrodes 112, 118 and 120, power source and microprocessor controller. It is noted however that the spaced electrodes are each independently variable in voltage and polarity. The respective upstream and downstream electrical sets 118 and 120 thus allow for a focusing and electrophoretic movement of charged reagents, somewhat analogous to a peristaltic wave. They can also serve as holding reservoirs as discussed with regard to the embodiment of FIGS. 1 and 2.

Also not indicated in FIGS. 3 and 4 is the amperometric apparatus which measures current flow through the sample electrode 112. Completion of a reaction in the cell is indicated by a plateauing of the current flow in the electrode. This amperometric determination allows easy interface of the cell with a microprocessor controlling the syringe drives responsible for introducing new reactants. The timing of the various steps within a cycle of a sequential step can thus be set according to the reaction kinetics in the particular combination of reactants in the cell.

EXAMPLE 1

1. APPARATUS

A simplified version of the apparatus shown in FIG. 2, but lacking the capillary electrophoresis interface, was utilized in this Example. The platinum electrode (46 in FIG. 2) with an affixed PVDF membrane for sample application (50 in FIG. 2) was 5 mm in diameter. One layer of cellulose paper (Whatman 3 MM, 5 mm diam.) was positioned over the PVDF to minimize diffusion of electrolytically generated reagents in the cell. The electrode was insulated (PTFE) so that electric current from the electrode passed through the PVDF. The electrode was positioned in the cell (4-ml glass vessel with a loose-fitting cap), together with a second simple platinum electrode wire. The electrodes were positioned 8 mm apart and connected to a constant power supply.

2. SAMPLE LOADING

The sample (200 picomoles β-lactoglobulin) was immobilized to the PVDF membrane (50), affixed to the sample platinum electrode (46) by passive means.

β-lactoglobulin is a 18-KDa protein with the following N-terminal sequence: $H_2$N-Leu-Ile-Val-Thr-(for details see Braunitzer, G. et al. (1972) Z. Physiol. Chemie, 353:832–834).

3. EDMAN DEGRADATION (a) COUPLING The cell was filled with 3.5 ml of butylchloride containing 5% (v/v) phenyl isothiocyanate, 5% (v/v) triethyl ammonium trifluoroacetate and 0.2% (w/v) dithiothreitol. The cell was flushed with argon, heated to 50° C. (air oven) and connected to a constant power supply (200 μA, 20–30 V) for 60 mins with the sample electrode (46) negative. The sample electrode was then removed from the cell, briefly washed (30 sec) with 0.5 ml ethylacetate and returned to the cell for the cleavage reaction.

(b) CLEAVAGE The cell was filled with 3.5 ml butylchloride containing 10% (v/v) trifluoroacetic acid and 0.2% (w/v) dithiothreitol, heated to 50° C. (air oven) and connected (sample electrode, positive) to the power supply (36 V, 50 μA) for 30 mins. The sample electrode was then removed from the cell.

4. DETERMINATION OF REMAINING N-TERMINAL RESIDUES

The PVDF membrane was removed from the sample electrode, washed with 0.5 ml ethyl acetate, and placed in the sample cartridge of an Applied Biosystems Sequencer (model 470A) equipped with an on-line phenylthiohydantoin (PTH)-amino acid analyzer. Sequence analysis of the N-terminal residues of the β-lactoglobulin remaining on the membrane was performed using regular Applied Biosystems cycles and program 03RTST. The sequencing results are shown in FIG. 5.

Figure 5:
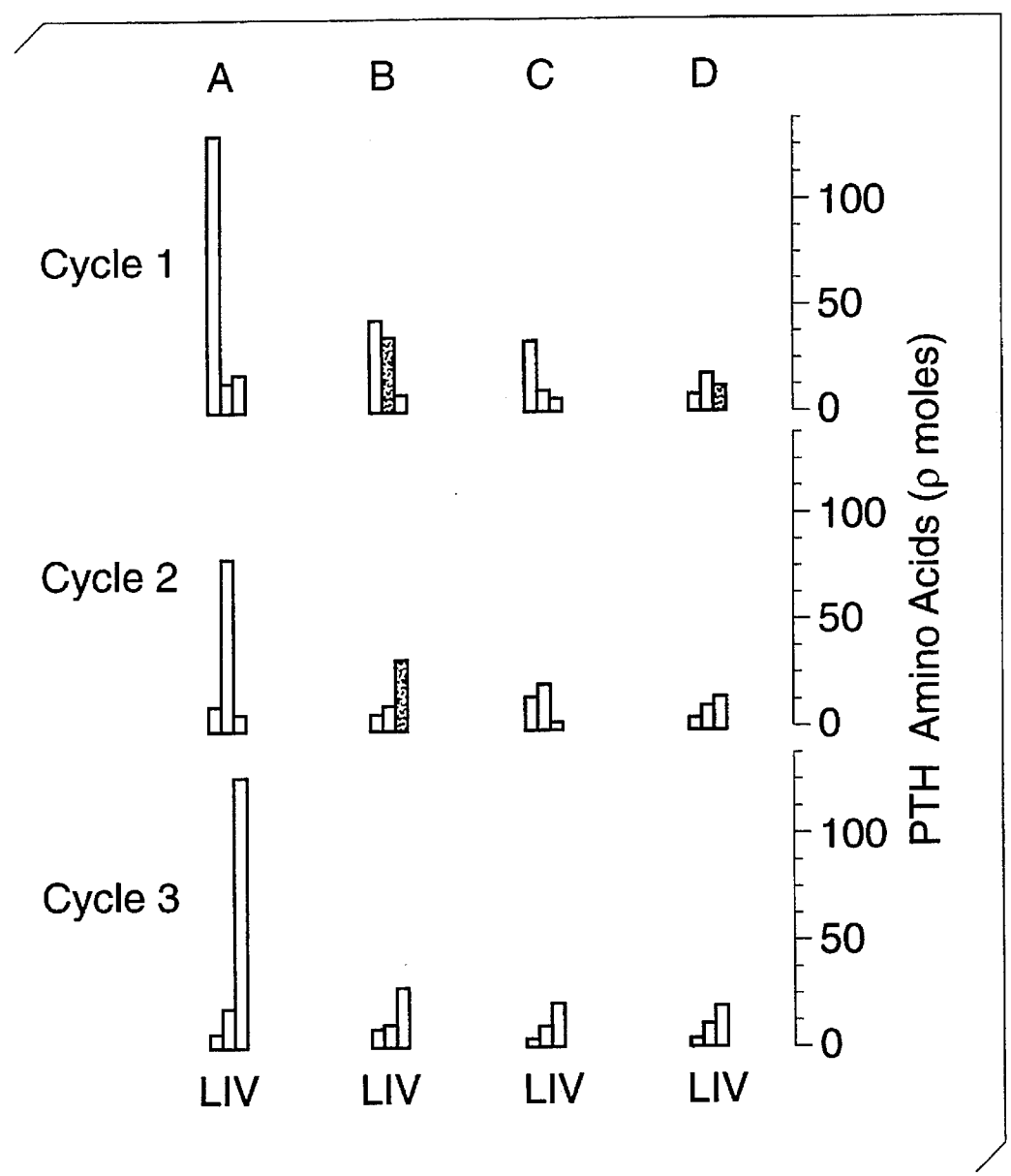
FIG. 5 is a graph depicting amino acid determination data of experiments A to D in Example 1.

Legend to FIG. 5:

A Control (β-lactoglobulin sequence was determined directly in 470A i.e. omitting step 3)

B One Edman degradation cycle was performed including electrolytic generation of the basic and acidic conditions required for coupling and cleavage and the remaining N-terminal residues sequenced in 470A C Control for 'B' (i.e., identical treatment as in B, but no electrolysis)

D Two Edman degradation cycles were performed electrolytically and the remaining N-terminal residues sequenced in 470A Note:

(1) One letter notation used for amino acids i.e., L, leucine; I, isoleucine and V, valine.

(2) Cycle 1, 2 and 3 in the leftmost legend corresponds to the first, second and third cycles of the 470A sequencing of the N-terminal residues remaining on the respective membrane.

5. COMMENTS (a) In Expt B; The presence of Ile in cycle 1, Val in cycle 2 (Thr in cycle 3 was too low to be detected) is clear evidence that the N-terminal leucine has been removed by the electrolytic coupling and cleavage procedure described in 3(a) and 3(b).

(b) confirmation that the removal of N-terminal leucine was due to the electrolytic process and not just due to passive exposure to the reagents is provided by the data in Expt C i.e., Compare Ile levels in cycle 1 (Val levels in cycle 2) in Expts B and C. In Expt C, β-lactoglobulin was exposed to the same regimen of chemicals as in B for the same time and temperature but no electrolysis was performed.

(c) In Expt D; The presence of increased levels of Val in cycle 1 is indicative of two successful cycles of Edman degradation having been performed by the electrolytic procedure described in 3(a) and 3(b) (i.e., compare Val level in Expt D with those in B and C-cycle 1).

(d) In the above described experiments NO attempt has been made to optimize the kinetics/chemistry of the coupling/cleavage processes.

EXAMPLE 2

This Example is similar in intent to Example 1 but performed on the micro/nano scale apparatus described by reference to FIGS. 3 and 4. The Example included the following experiments:

(A) Control

Summary

β-lactoglobulin is adsorbed to sample matrix and then sequenced using a standard ABI 420 Sequencer.

Procedure

β-lactoglobulin adsorbed onto PVDF disc 0.8 mm diameter 0.15 mm thick. PVDF discs (≈50) prewetted in acetonitrile then immersed in 1 ml 10% acetonitrile 10 mgm β-lactoglobulin for 1 hour at 20° C. Protein solution poured off the discs, washed 10 times (≈5 ml) 10 % acetonitrile. Discs washed 10 times in water then dried in freeze dryer stored under argon at −20° C. One disc placed into ABI 470 Sequencer with preconditioned polybrene glass disc. Normal PTH cycles.

(B) Example of Electrolytic Coupling

Summary

β-lactoglobulin is adsorbed to sample matrix and the matrix is disposed in the microcell of FIGS. 3 and 4. PITC Edman reagent is introduced to the microcell where basic conditions are electrolytically generated in situ. The sample matrix is then sequenced with ABI 470.

Procedure

β-lactoglobulin PVDF disc prepared as in (A) is placed in the microcell. PITC Edman reagent is injected as 5% PITC, 5% TEAFTA (triethylammonium trifluoroacetate) and 0.01% DTT in butyl chloride. The sample electrode is charged negatively, with both proximal electrodes 128, 130 positive, 15 volts 0.6 µA to achieve coupling of the PITC with the N-terminal amino acid. Charge is maintained for 30 minutes while the temperature is kept at 50° C. The sample disc is washed with 100 µl butyl chloride then removed from microcell and placed into ABI 470 Sequencer with preconditioned polybrene disc. Program started at O3CPTH step 15 (no coupling in first cycle, only washes and cleavage).

(C) Example of Electrolytic Coupling and Cleavage

Summary

β-lactoglobulin PVDF disc placed in microcell, PITC introduced and electrolytically coupled as (B) above then polarity reversal to produce conditions for cleavage of terminal amino acid. The sample matrix is then sequenced with ABI 470.

Procedure

β-lactoglobulin PVDF disc prepared as in (A), placed into microcell, coupled with PITC as detailed for (B), washed with 100 µl butyl chloride then cleaved in microcell as follows: 10% trifluoro-acetate, 0.01% DTT in butyl chloride introduced to the cell. Sample electrode made positive, both proximal electrodes 128, 130 negative. Temperature maintained at 50° C. 15 minutes of 15 volts, 0.6 µA. Sample disc washed with 100 µl butyl chloride then removed from microcell and placed into ABI Sequencer with a preconditioned polybrene disc (normal O3CPTH cycles used).

(D) Control for (C)

Summary

PITC introduced, but basic and acidic conditions not electrolytically generated, sample matrix sequenced with ABI 470.

Procedure

Exactly the same as (C) except no electrical current used in the microcell. Same coupling and cleavage reagents, time and temperature.

(E) Example of Electrophoretic ITC Introduction and Electrolytic Coupling and Cleavage Summary β-lactoglobulin PVDF disc placed in microcell, rhodamine ITC electrophoretically focused onto the sample matrix. Basic conditions electrolytically generated to promote coupling then acid conditions to achieve cleavage. Sample matrix then sequenced with ABI 470.

Procedure

β-lactoglobulin PVDF disc prepared as in (A) placed into microcell. Coupling achieved by injecting 10 mg rhodamine ITC, 5% TEAFTA, 0.01% DTT in 5 ml butyl chloride. Sample electrode held negative 15 volts, 0.7 µA for 30 minutes with both proximal electrodes positive. Temperature maintained at 50° C. Cell washed with 100 µl butyl chloride then cleaved as described for (C). Cell washed with 100 µl butyl chloride. Disc removed from microcell and placed into ABI 470 Sequencer with preconditioned polybrene disc (normal O3CPTH cycles).

Figure 6:
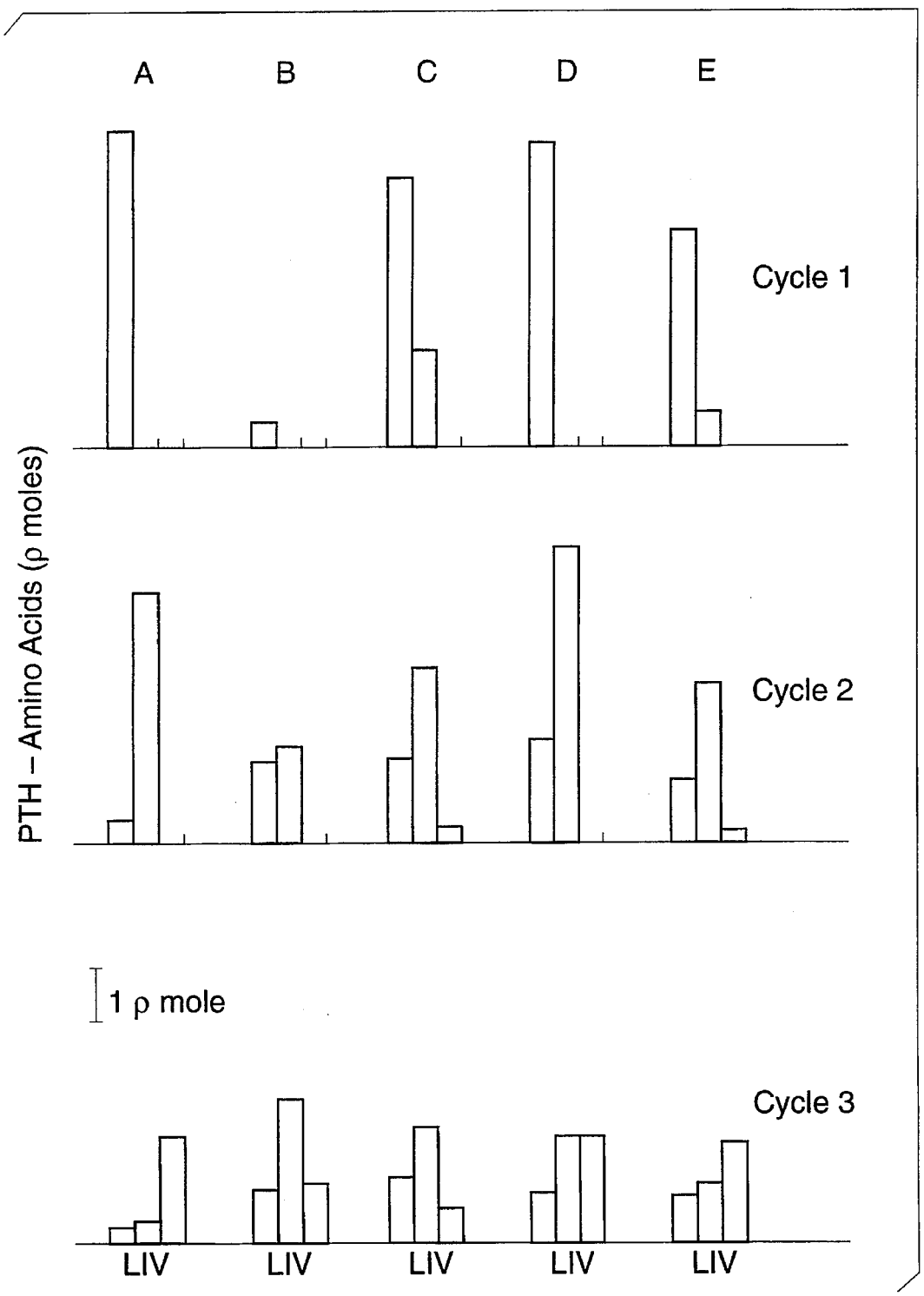
FIG. 6 is a graph depicting amino acid determination data of experiments A to E in Example 2.

The data from each of experiments A to E above are depicted on FIG. 6, expressed as picomoles, PTH-amino acids released per cycle (1 letter amino acid codes). Three cycles of the ABI 470 were undertaken (i.e. the three N-terminal amino acids of the β-lactoglobulin remaining on the sample matrix were identified).

Referring to FIG. 6, reading control (A) downwards through the three cycles, the N-terminal sequence is clearly Leu-Ile-Val.

In experiment (B), the presence of Leu at cycle 1 indicates coupling (but not cleavage) of PITC to the β-lactoglobulin. At cycle 3 however it is apparent that all three amino acids survived the initial electrolytic coupling reaction of PITC to L.

In experiment (C), electrolytic coupling and cleavage), the thing to note is the presence of a relatively large Ile figure in the first cycle. (The Leu reading merely indicates non optimal cleavage of this experimental system.) The presence of an Ile reading in the first cycle of the remaining amino acids on the sample matrix clearly shows that cleavage of the end terminal L has been effective. Similarly the Val reading in the second cycle, shows that Ile was the terminal amino acid.

Experiment (D), the control for experiment (C), indicates that without energizing of the electrode, truncation of the terminal amino acids does not take place.

In experiment (E), as with (C) above, the presence of Ile in the first cycle and Val in the second cycle indicates that the electrophoretic/electrolytic coupling/cleavage successfully removed the terminal amino acid.

Although the invention has been illustrated by reference to the Edman degradation sequencing of a protein, the application of electrophoretic transfers of a chemical reactant to or from an immobilized first reactant and/or electrolytic activation of reactants may be applicable to other sequencing and/or sequential chemical reactions, such as the construction of macromolecules. Furthermore, apparatus in accordance with the invention may have a plurality of spaced storage loci by providing a plurality of electrodes spaced from the reaction locus and under the control of appropriate electric voltages.

EXAMPLE 3

Development of Liquid Chromatography System
Chemicals:

Recombinant murine interleukin-6 (mIL-6) was produced by over expression in *Escherichia coli* and purified as previously published (Simpson et al *Biochem. Biophys. Res. Commun* 157: 364–372, 1988). Chick egg lysozyme, bovine serum albumin, ribonuclease A, myoglobin, carbonic anhydrase and ovalbumin were purchased from Sigma (St. Louis, Mo., U.S.A.). *Staphylococcus aureas* V8 protease was from Miles Scientific (Naperville, Ill., U.S.A.).

HPLC-grade organic solvents were purchased from Mallinckrodt (Melbourne, Australia). Trifluoroacetic acid (Sequenal grade) was from Pierce (Rockford, Ill., U.S.A.). Polished, deionised water was obtained from a tandem Milli-RO15 and Milli Q system (Millipore, Bedford, Mass., U.S.A.). Ammonium bicarbonate (AnalAR grade) was purchased from British Drug Housed (Poole, U.K.).
Chromatographic Systems:

Conventional HPLC: The following chromatographic equipment was employed during the development of the present invention:

(i) A Hewlett-Packard (Waldbronn, Germany) liquid chromatograph (HP 1090A), equipped with an autosampler and diode array detector (HP 1040A). Spectral and chromatographic data were stored on electronic disc, using a Hewlett-Packard HP-85 computer and a Model 9153 disc drive. Manual injections were performed with a Rheodyne (Cotati, Calif., U.S.A.) Model 7125 injector, equipped with a 2-mL injection loop, installed in the column oven compartment, and (ii) an Applied Biosystems (Foster City, Calif., U.S.A.) liquid chromatograph (Model 120A) equipped with a Rheodyne Model 8125 injector installed in the column oven compartment.

Capillary HPLC: A schematic diagram of the two capillary HPLC systems used in the development of the present invention is shown in FIG. 1. System 1—The solvent delivery for this system was supplied by an Applied Biosystems Model 120A liquid chromatograph. Accurate low flow rates (2–5 µl/min.) through the capillary columns and reproducible gradient formation were achieved with a pre-injection solvent split that diverted most of the solvent flow through approximately 100 cm of 0.1-mm I.D., 0.26-mm O.D. fused silica tubing (S.G.E., Melbourne, Australia) at an Upchurch (Oak Harbor, Wash., U.S.A.) ¹⁄₁₆-in tee (P/N U-428). Capillary columns were directly connected to a Rheodyne Model 8125 injector fitted with 0.5–5 µl injection loops. The flow through the column could be adjusted to 3–5 µl/min. by the splitter from a pump flow rate of 100–200 µl/min. With this split-flow approach, frequent monitoring of the actual flow through the capillary column is necessary. This is readily achieved by applying a 10 µl chromatography syringe (Microliter 700 Series, Hamilton, Reno, Nev., U.S.A.) to the effluent and accurately timing the advancing emniscius with a stop watch. For detection, the conventional flow cell was replaced with a 6-mm optical pathlength "U"-shaped longitudinal capillary flow cell (LC Packings, Amsterdam, The Netherlands).

System 2—The solvent delivery system was a Hewlett-Packard HP1090A liquid chromatograph. Accurate solvent delivery rates and gradient formation were achieved as described for System 1. Capillary columns were directly connected to a Rheodyne Model 7520 injector fitted with 0.2–1.0 µl internal sample rotors. A "U"-shaped longitudinal capillary flow cell (6-mm path length, illuminated volume, approximately 26.5 nl) installed in a conventional Spectra-Physics forward-optics scanning detector flow cell holder (LC Packings, Amsterdam, The Netherlands), was used for eluate detection. Data collected were either sent to a strip-chart recorder via the single wavelength mode or collected on an IBM PS/2 computer (Model P70 386) with Spectra Focus software installed and operated in the multiple-wavelength mode (195–340 nm, 5-nm intervals).
Column Supports:

The following packing materials were used during the development of the present invention:

(a) Brownlee RP-300 $C_8$ (7-µm dp, dimethyloctyl silica, 300 Å pore size, packed into 30×4.6 mm I.D. and 30×2.1-mm I.D. cartridges), obtained from Applied Biosystems. Brownlee RP-300 $C_8$ packed into a 50×0.32 mm I.D. glass-lined column was provided by LC Packings (Amsterdam, The Netherlands), (b) Applied Biosystems PTH-C18 packed into a 150 mm×0.32 mm I.D. glass-linked column was supplied by LC Packings, and (c) Brownlee RP-300 $C_8$ packed into fused silica capillary tubing as described below.

Fused-Silica Capillary Column Construction:

Microcolumns of 0.32 mm I.D. were constructed in the following manner. A 20-mm length of 0.420-mm O.D.× 0.320-mm I.L. polyimide-coated fused-silica tubing (Polymicro, Phoenix, Ariz., U.S.A.) was used as a disc cutter to fabricate internal column frits from 0.45 µm porosity hydrophilic polyvinylidine difluoride (PVDF) (Cat. #HVLOP 04700 Millipore, Bedford, Mass., U.S.A.). Using a length of 0.275 mm O.D.×0.075-mm I.D. polyimide-coated fused silica, the frit was inserted into a 60-mm length of polyimide-coated fused silica (Polymicro, Pheonix, Ariz., U.S.A.) to a depth of 5 mm. A small bead of epoxy resin (E-Pox-E Glue, "Loctite", Knoxfield, Vic., Australia)—the resin was pre-cured by stirring whilst applying heat with a heat gun until a tacky consistency was achieved—was then applied to the join and gentle heating was continued until the epoxy resin had fully cured. Proper precuring of epoxy glue is important to ensure that it does not run up the capillary and, thereby, block the frit (Shelly et al. Anal. Chem. 56: 2990–2992, 1984).

Once the PVDP frit had been positioned in the fused-silica capillary column, a slurry-packing procedure was employed to pack the column. The slurry reservoir consisted of an empty 50 mm×2 mm I.D. stainless-steel glass-linked tube (SGE, Ringwood, Victoria, Australia) with standard ¼" column endfittings (Alltech, Dearfield, Ill., U.S.A.) that had 0.5 mm I.D. holes as flow-through ports. The fused-silica capillary column was connected to the standard ¼" column endfitting, either by minitight fittings (Upchurch, P/N F-218) or by a teflon tubing sleeve (see FIG. 1B). Brownlee RP-300 7-µm dp, 300 Å pore size, dimethyloctylsilica (600 mg) was obtained by unpacking a 30 mm×4.6 mm I.D. cartridge (Applied Biosystems, P/N 0711-0055). A slurry of this material in n-propanol (20 mg/500 µl) was sonicated for 15 min. in a 1.5-ml polypropylene tube. Before packing, the capillary column was filled with packing solvent (n-propanol) using a column-packing pump (Shandon, Cheshire, U.K.) at a pressure of 100 bar. This step pre-filled the column with packing solvent and also allowed the system to be checked for leaks. The slurry reservoir was then emptied and quickly replaced with 200 μl of the prepared packing-slurry mixture. The column was packed at a constant pressure of 100 bar for 16 h and then conditioned with 50% (v/v) aqueous methanol for a further 4 h at the same pressure. The capillary column was then carefully dismantled and plugged by inserting the bottom end into a silica on rubber septa and placing a closed-off 1/16" stainless-steel zero-dead-volume union (Swagelock, Solon, Ohio, U.S.A.) on the top of the column. Column efficiency was tested using a series of standard proteins (Ribonuclease A, lysozyme, bovine serum albumin, myoglobin, carbonic anhydrase and ovalbumin).

Peptide Mapping:

Recombinant mIL-6 (120 μg) in 200 μl of 1% (w/v) ammonium bicarbonate containing 0.01% (w/v) Tween 20 was digested with *Staphylococcus aureus* V8 protease at an enzyme/substrate mass ratio of 1:20 at 37° C. for 18 h.

Protein Determination:

Lysozyme (ca/mg) was dissolved in 1-ml water and the protein concentration was accurately determined by measuring the absorbance at 281.5-nm using a $E^1_{281.5\ nm}$ value of 26.4 (Aune and Tanford *Biochem* 8; 4579–4585, 1969).

Peptide Synthesis:

Peptides were synthesised on an Applied Biosystems peptide synthesizer (Model 430A) using 2-(1H-benzotriazol-1-yl)-1,1,3,3,tetramethyluronium tetrafluoroborate (TBTU) for the coupling of Boc-amino acids as elsewhere described (Reid and Simpson, *Anal. Biochem.* In press)

EXAMPLE 4

Figure 7A:
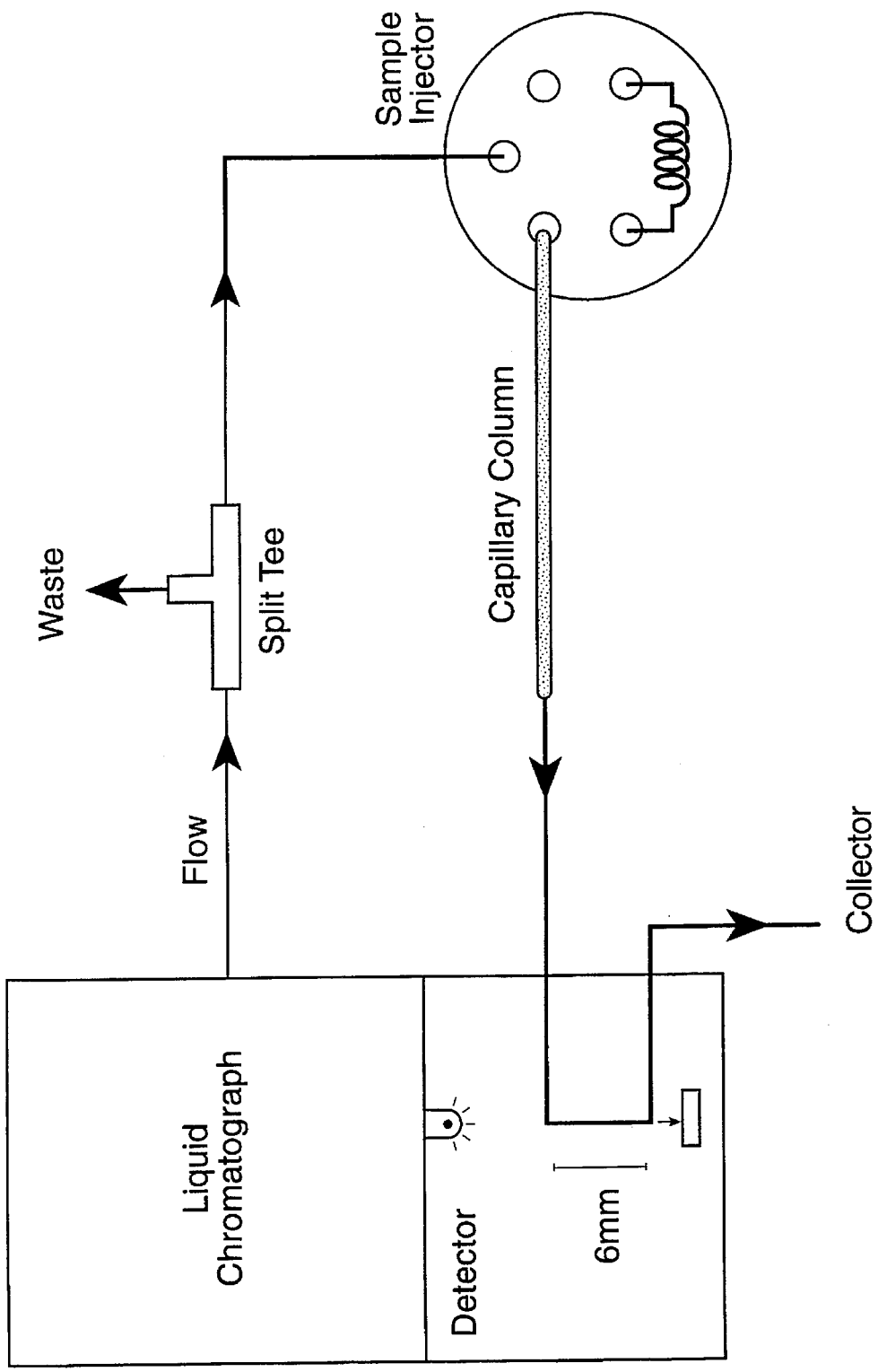

This example refers to FIGS. 7 to 16 in which:

FIG. 7 is a schematic diagram of the gradient capillary HPLC used in accordance with the present invention.

A: System 1 consisted of an Applied Biosystems Model 120A liquid chromatograph and, System 2 consisted of a Hewlett-Packard Model 1090A liquid chromatoraph equipped with a spectra-physics SPECTRA FOCUS SYSTEM variable wavelength detector. Further details of the systems are given in Example 3.

B: Capillary column;

C: Split-flow device;

D: Zero-dead-volume tubing union.

1, Chromatographic stationary phase; 2, Standard 1.59-mm (1/16") stainless-steel ferrule; 3, Standard 1.59-mm (1/16") stainless-steel male nut; 4, Teflon tubing 1.59mm (1/16") O.D.×0.5-mm I.D. (Beckman, Melbourne, Australia); 5, Polyimide coated fused silica 0.42-mm O.D.×0.32-mm I.D. capillary tubing; 6, Polyimide coated fused-silica 0.275-mm O.D.× 0.075-mm I.D. capillary tubing; 7, Hydrophilic polyvinylidine difluoride frit, 0.32-mm diameter, 0.45-μm pore size; 8, epoxy resin; 9, Teflon tubing 20-mm×1.59-mm (1/16") O.D.× 0.05-mm I.D. (SGE, Ringwood, Vic., Australia); 11, Standard stainless-steel tee 1.59-mm (1/16") with 0.5-mm flow ports; 12, PEEK tubing 1.59-mm (1/16") O.D.×0.178-mm I.D. (Upchurch, Oak Harbor, Wash., U.S.A.); 13, Teflon tubing 1.59-mm (1/16") O.D.×0.25-mm I.D.; 14, Polyimide coated fused-silica 0.26-mm O.D.×0.1-mm I.D. capillary tubing (SGE, Ringwood, Vic., Australia).

FIG. 8 is a graphical representation showing the effect of column internal diameter and flow rate in detector sensitivity. Chromatographic conditions: column support, Brownlee RP-300 $C_8$ (7-μm dp, dimethylocryl silica, 300 Å pore size, 30-mm×4.6-mm I.D. and 100-mm×2.1-mm I.D., Applied Biosystems, and 50-mm×0.32-mm I.D. packed by the inventors—see Example 3); linear 60-min. gradient from 0–100% B where eluent A is 0.1% (v/v) trifluoroacctic acid and eluent B is 60% acetonitrile/40% water containing 0.1% (v/v) trifluoroacctic acid. Column temperature, 45° C.; detection, 215-nm; flow rates, 1 ml/min., 200 μl/min. and 4 μl/min. for 4.6-mm I.D., 2.1-mm I.D., and 0.32-mm I.D. columns, respectively. Sample, lysozyme (varying concentrations).

Figure 9:
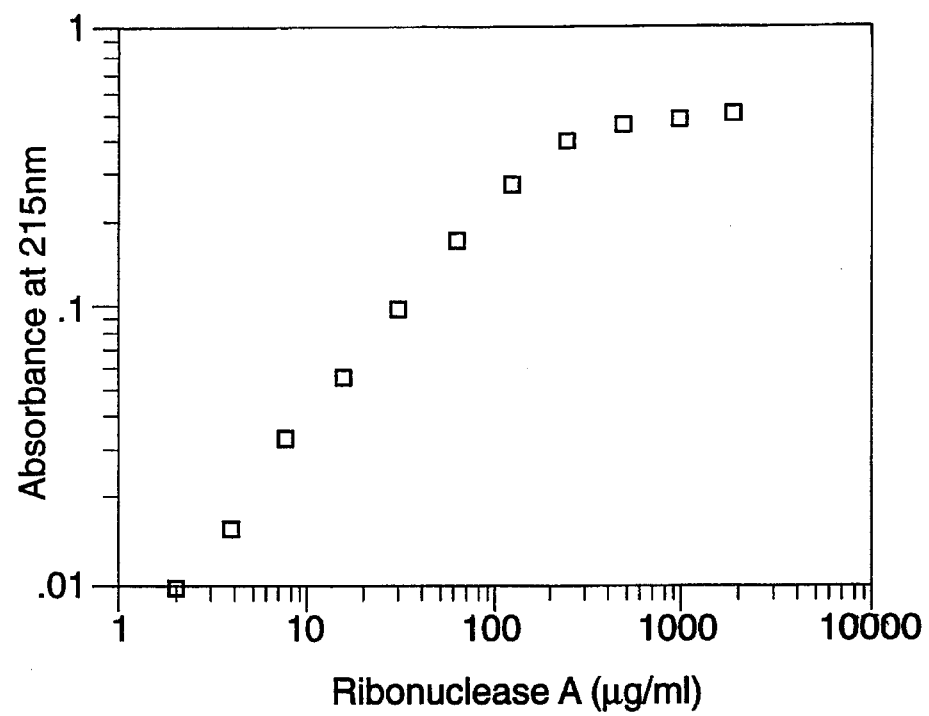
FIG. 9 is a graphical representation showing linearity of detector response for ribonuclease A injected directly into the longitudinal capillary flow cell. The calibration curve is presented in log-log format.
Figure 10A:
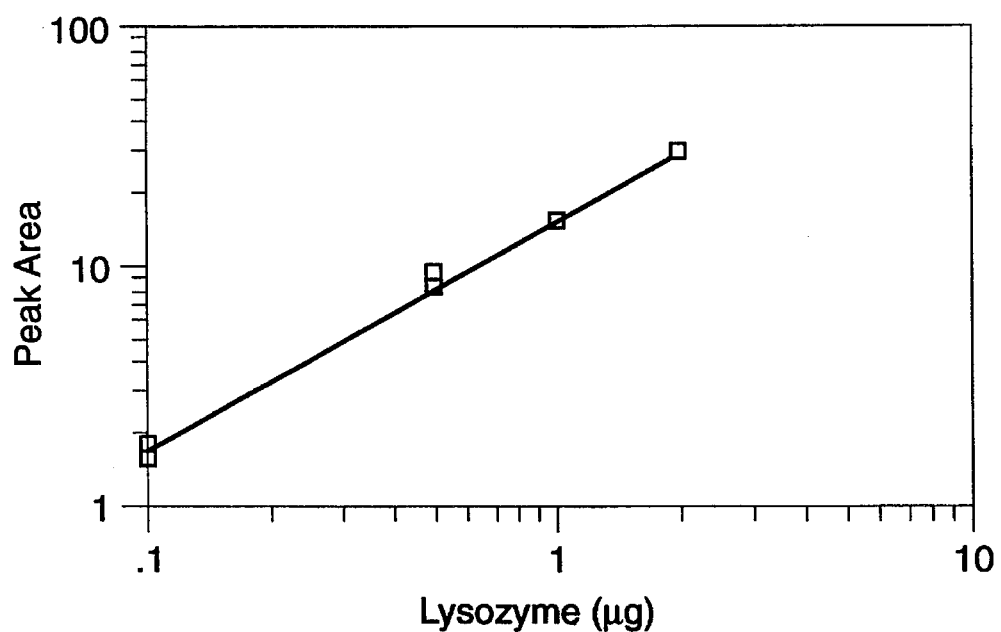
FIGS. 10A–10D are a graphical representation showing linearity of detector response for lysozyme chromatographed on a 50-mm×0.32-mm I.D. Brownlee RP-300 column (LC Packings).
Figure 10D:
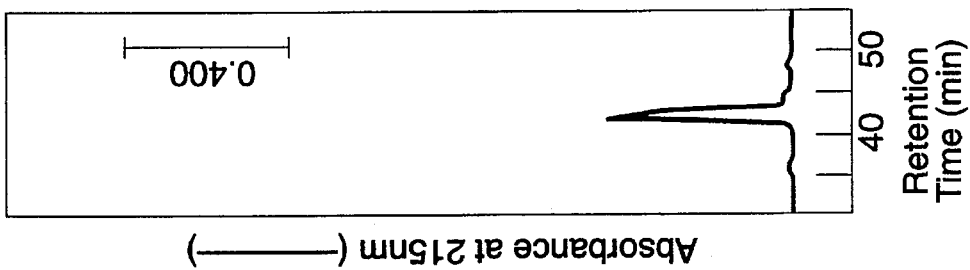
Figure 10C:
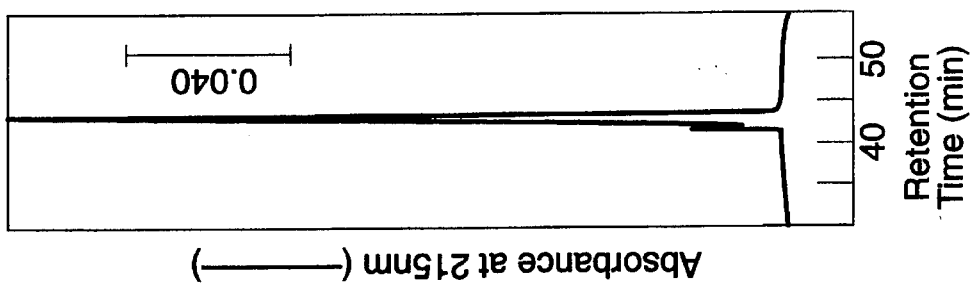
Figure 10B:
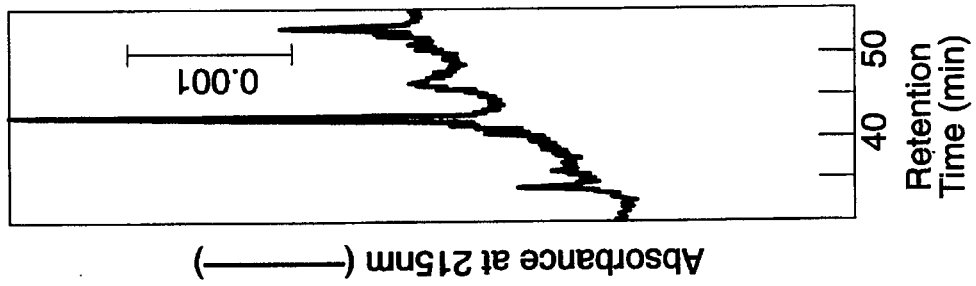

FIG. 9 is a graphical representation showing linearity of detector response for ribonuclease A injected directly into the longitudinal capillary flow cell. The calibration curve is presented in log-log format.

FIG. 10 is a graphical representation showing linearity of detector response for lysozyme chromatographed on a 50-mm×0.32-mm I.D. Brownlee RP-300 column (LC Packings). The liquid chromatograph system 1 described in Example 3 was used in this invention. Elution conditions were identical to these described for the 0.32-mm I.D. column in FIG. 8. Progressively higher amounts of lysozyme were chromatographed in duplicate and average peak area values *(arbitrary units) at each concentration are plotted (panel A). Representatives chromatograms for 500 pg (panel B), 100 ng (panel C) and 2 μg of lysozyme (panel D) are shown so that the practical limits of sensitivity can be assessed.

Figure 11:
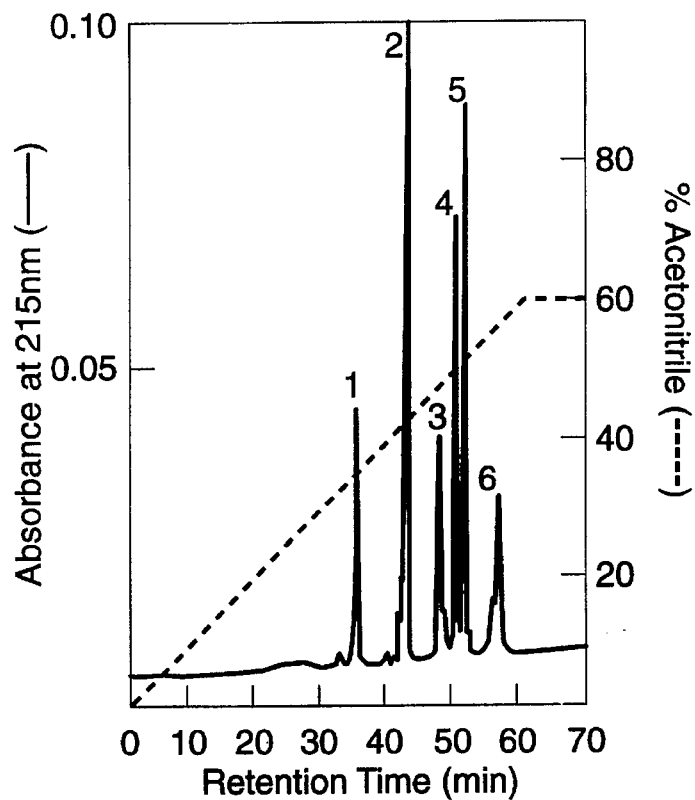
FIG. 11 is a graphical representation depicting separation of protein standards on a Brownlee RP-300 column (50× 0.32-mm I.D.).

FIG. 11 is a graphical representation depicting separation of protein standards on a Brownlee RP-300 column (50× 0.32-mm I.D.). This column was slurry-packed by us as described in Example 3. Chromatographic conditions: the column was developed with a linear 60-min. gradient from 0 to 100% B, where solvent A was 0.1% (v/v) trifluoroacetic acid and solvent B was 60% acetonitrile/40% water containing 0.1% (v/v) trifluoroacetic acid. Column temperature, 45° C. Flow rate, 3.6 μl/min. Protein standards: 1, ribonuclease A, 2, lysozyme; 3, bovine serum albumin; 4, carbonic anhydrase; 5, myoglobin; 6, ovalbumin, Sample load, 50 ng in 0.5 μl water.

Figure 12:
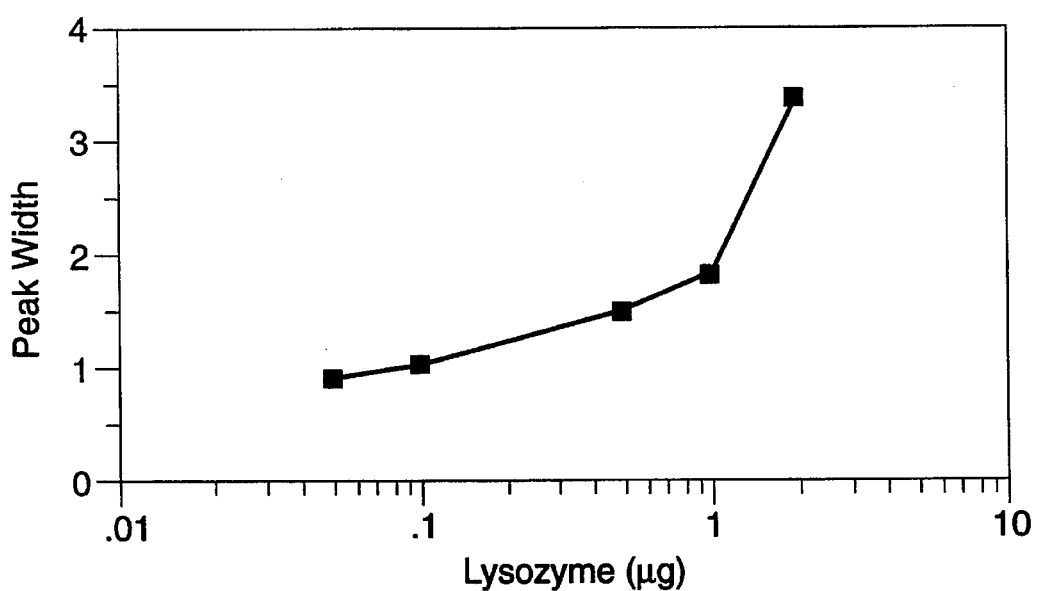
FIG. 12 is a graphical representation depicting the effect of protein load on peak width of eluted lysozyme for a 50-mm×0.32-mm I.D. column (Brownlee RP-300).

FIG. 12 is a graphical representation depicting the effect of protein load on peak width of eluted lysozyme for a 50-mm×0.32-mm I.D. column (Brownlee RP-300). Values are the average of two experiments. Chromatographic conditions were the same as these described in FIG. 11. Peak widths (mm) were measured at peak half heights.

Figure 13A:
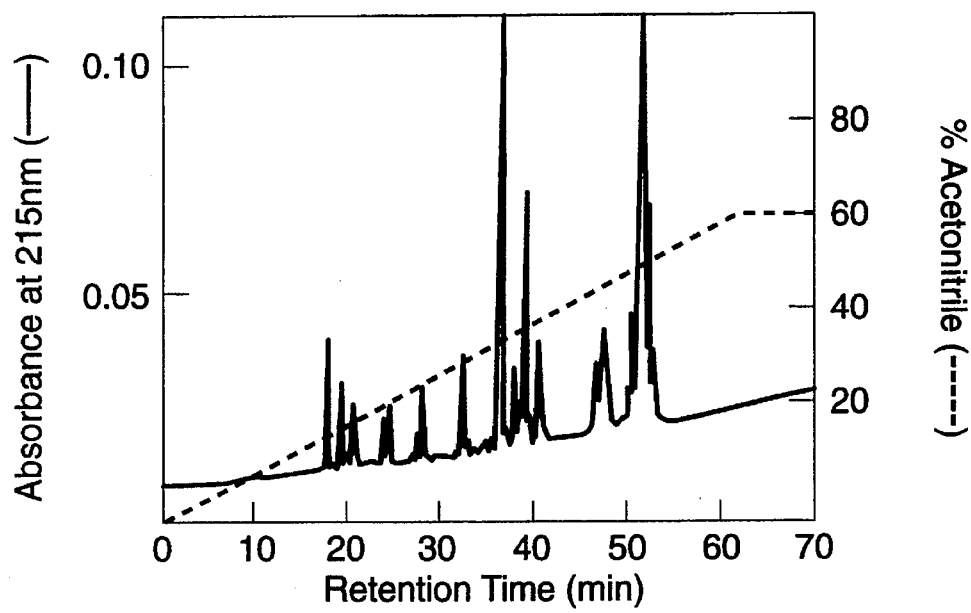
FIG. 13 is a graphical representation of high-sensitivity peptide mapping of recombinant mIL-6 using 0.32 I.D. (reversed-phase) capillary columns.
Figure 13B:
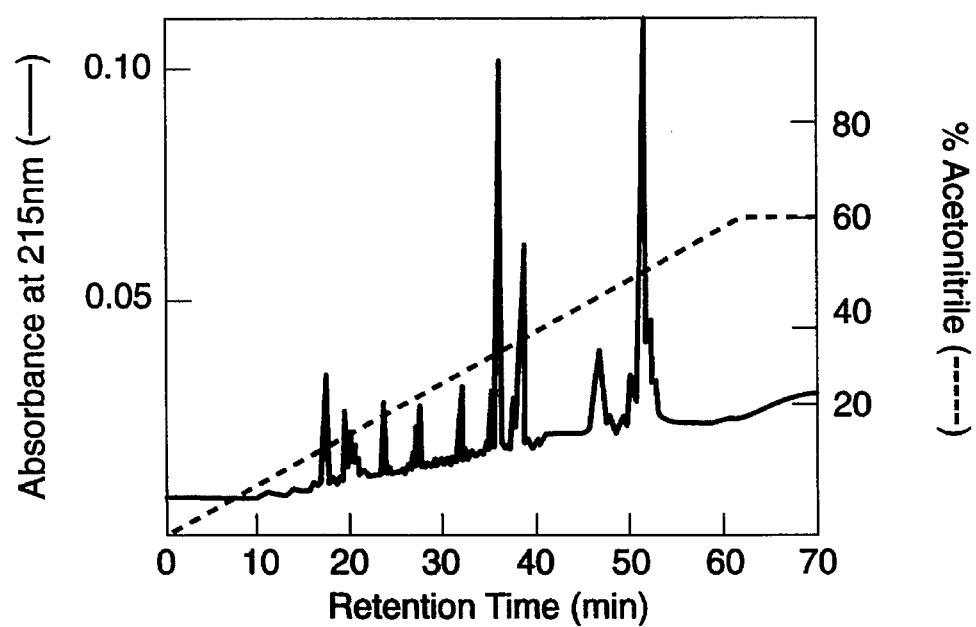
Figure 13C:
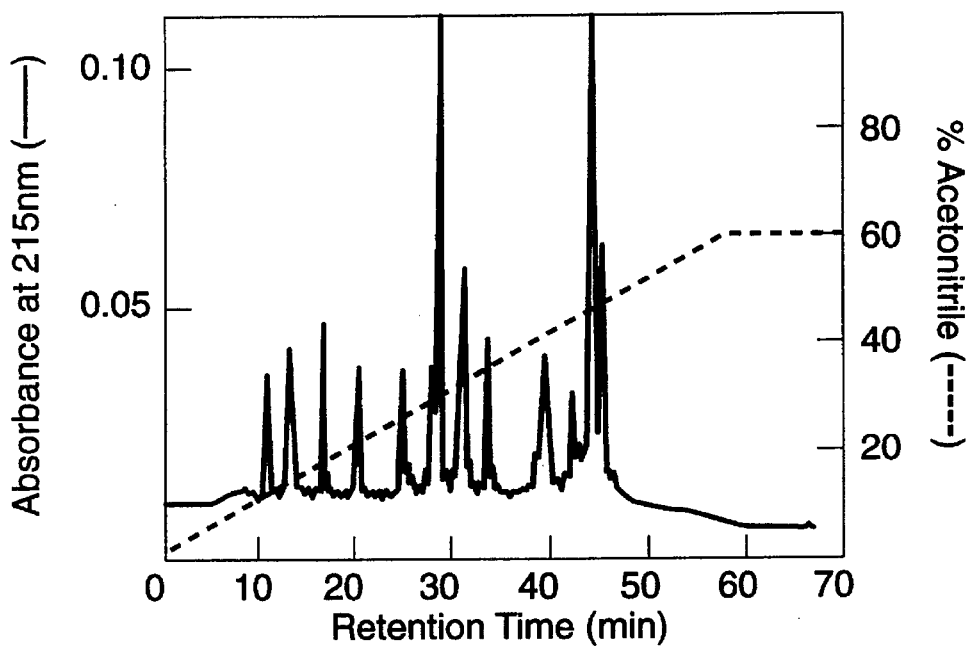
Figure 14A:
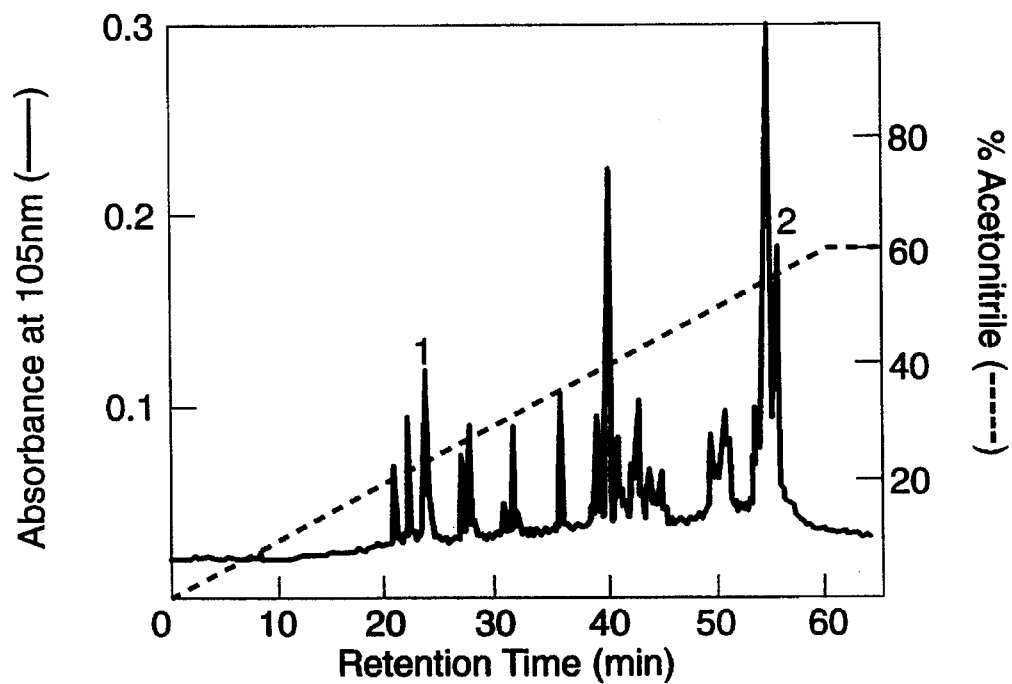
FIG. 14 is a graphical representation showing multiple-wavelength detector performance.
Figure 14B:
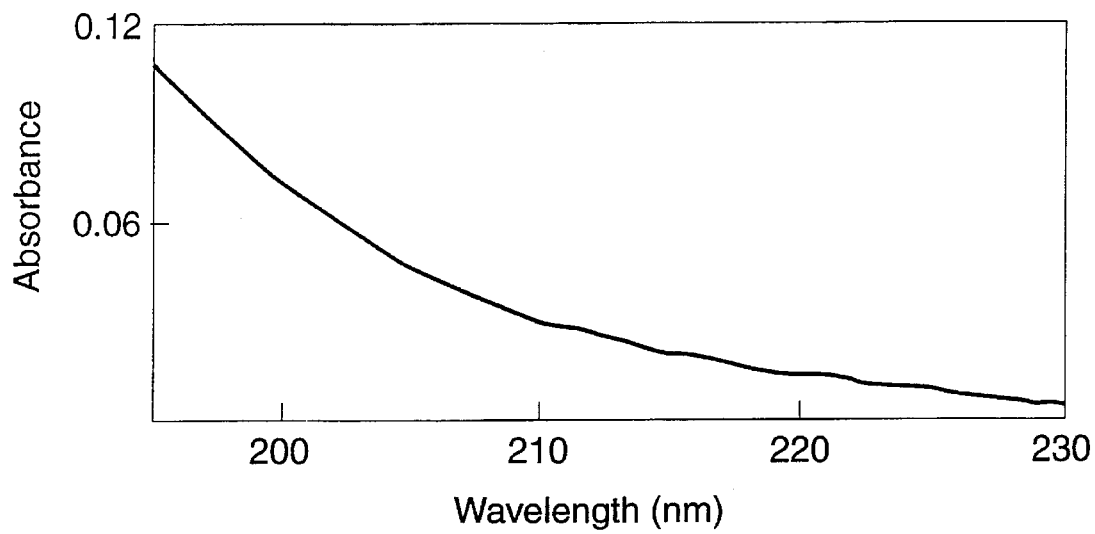
Figure 14C:
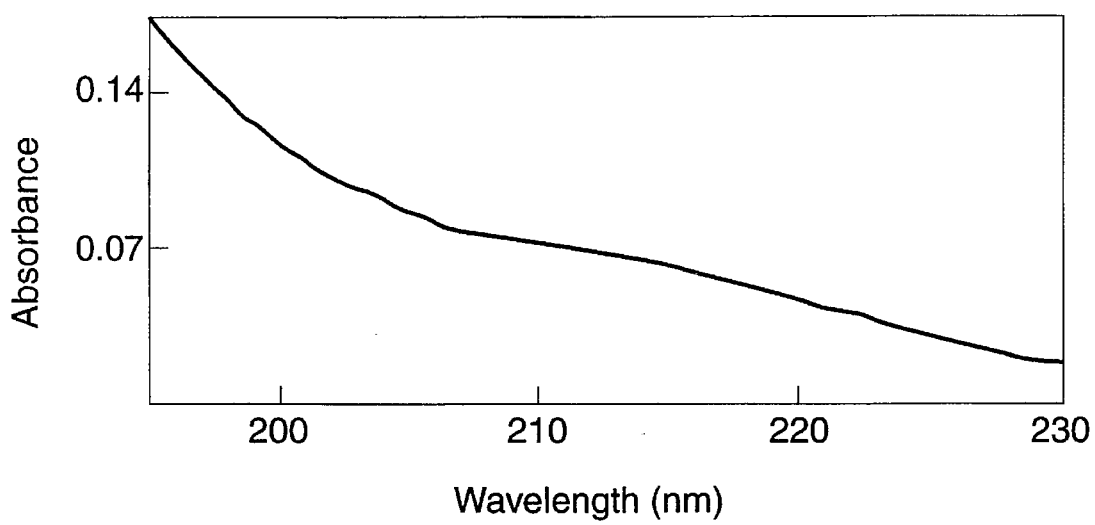
Figure 14D:
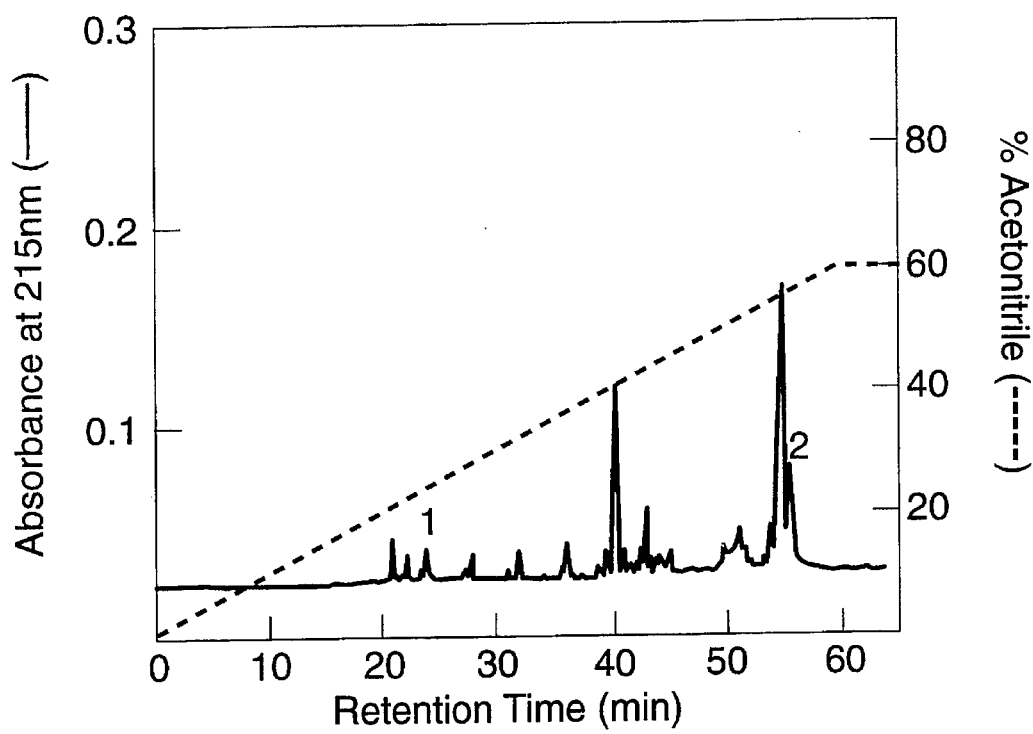
Figure 14E:
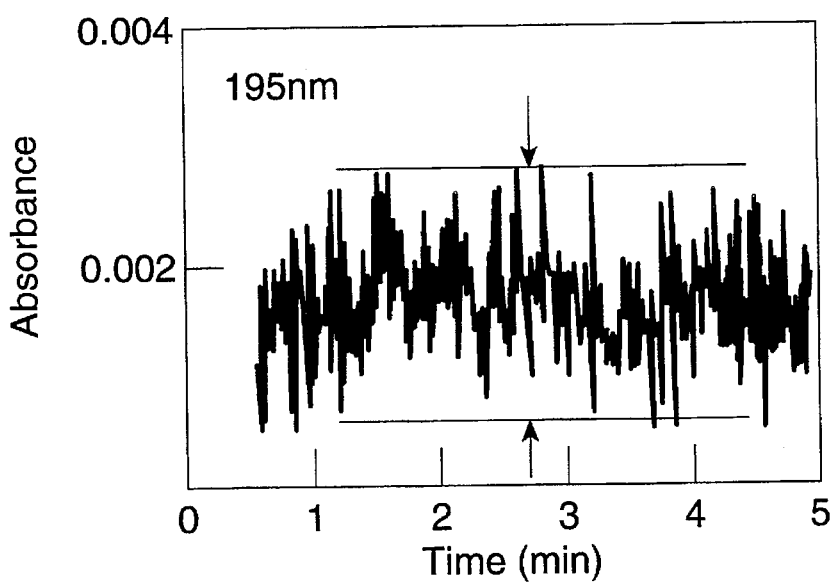
Figure 14F:
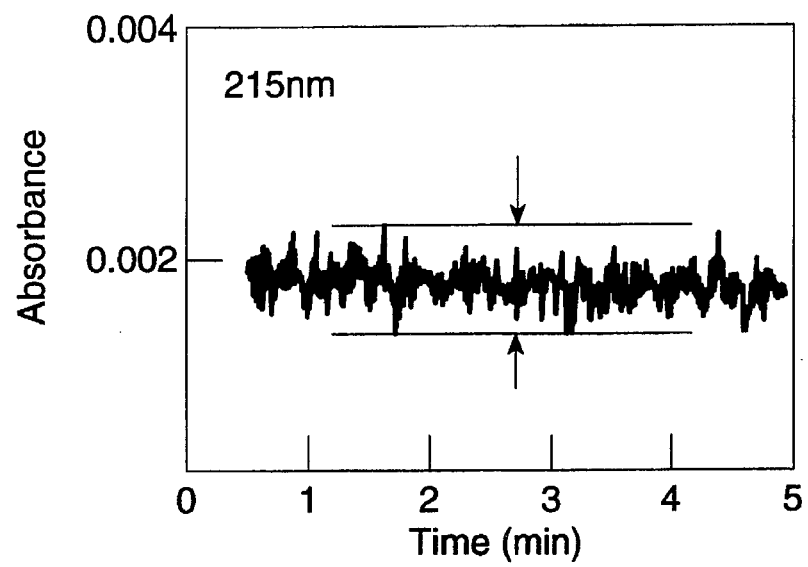

FIG. 13 is a graphical representation of high-sensitivity peptide mapping of recombinant mIL-6 using 0.32mm I.D. (reversed-phase) capillary columns. Chromatographic conditions: support, Brownlee RP-300 (7-μm dp dimethyloctyl silica, 300 Å pore size). Elution conditions were the same as those described in FIG. 11. Panel A, 50-mm×0.32-mm I.D. fused-silica column packed by us (see Experimental); Panel B, 50-mm×0.32-mm I.D. glass-lined column packed by LC Packings (Amsterdam, The Netherlands); Panel C, 30-mm ×2.1-mm I.D. cartridge (Applied Biosystems, Foster City, Calif., U.S.A.). Sample load: panels A and B (200 ng of digest, 10 pmol), panel C (5 μg of digest, 350 pmole). Flow rate: 0.32 mm I.D. columns (panels A and B). 3.6 μl/min; 2.1-mm I.D. column (panel C), 178 μl/min.

FIG. 14 is a graphical representation showing multiple-wavelength detector performance. Sample: *S.aureus* V8 protease digest of murine IL-6 (mIL-6) (200 ng). Chromatographic conditions: 100×0.32-mm I.D. Brownlee RP-300 column packed as per Example 3 and operated as described in FIG. 11. Detector: Spectra-Physics, Spectra Focus fitted with a 6-mm optical pathlength longitudinal capillary flow cell (LC Packings, Amsterdam, The Netherlands). Panels A and B, detection at 195-nm and 215-nm, respectively; panels C and D, spectral analysis of peaks 1 and 2, respectively; panels E and F, baseline noise at 195-nm and 215-nm, respectively.

FIG. 15 is a graphical representation showing a spectral analysis of aromatic amino acid-containing synthetic peptides chromatographed by reversed-phase capillary liquid chromatography. Spectral data were obtained using a multiple-wavelength detector (Spectra Physics) fitted with a 6-mm optical pathlength longitudinal capillary flow cell (LC Packings). Chromatographic conditions are given in FIG. 14. Panel A, 0.32 mm I.D. capillary column profile of synthetic peptides AB205 (SRDMYMESEGGDGY) and AB209 (DLAWWELR); panel B, multiple signal plot of data shown in panel A; panels C and D, zero-order-(_____) and second-order-derivative spectra (----) of synthetic peptides AB205 and AB290, respectively. Sample load, 250 ng.

Figure 16:
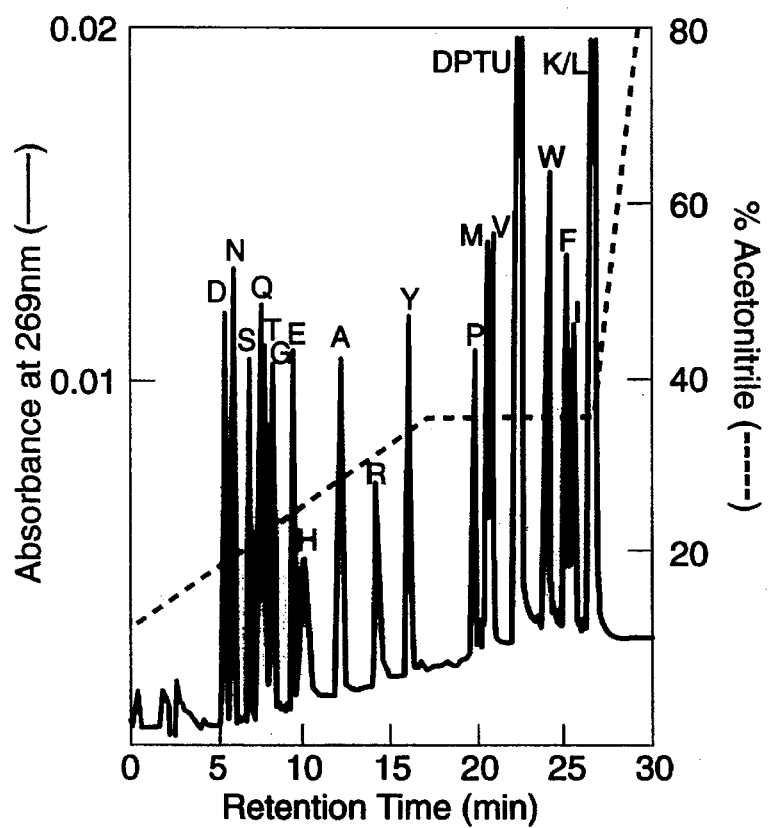
FIG. 16 is a graphical representation showing separation of phenylthiohydantoin-amino acids by reversed-phase capillary liquid chromatography.

FIG. 16 is a graphical representation showing separation of phenylthiohydantoin-amino acids by reversed-phase capillary liquid chromatography. Chromatographic conditions: column, 150-mm×0.32- mm I.D. Applied Biosystems PTH-C18 (packed by LC Packings). Solvent A, 8.3 mM Na acetate, 5% (v/v) tetrahydrofuran, pH 4.1; solvent B, acetonitrile. Column temperature, 55° C. Flow rate, 5 µl/min. Sample load: a 1 pmole mixture of PTH-amino acids in 0.5 µl 2% (v/v) aqueous acetonitrile. Capillary liquid chromatography configuration, system 1 (see FIG. 7 and Example 3). PTH-amino acid notation is shown using the one-letter code for amino acids; DPTU, diphenylthiourea.

Capillary Column Performance:

For efficient operation of capillary columns (≦0.32-mm I.D.), both the flow rate and detector volumes have to be substantially reduced compared to microbore and large-bore liquid chromatography. The capillary liquid chromatograph system used in accordance with the present invention was designed to achieve accurate low flow rates (3–5 µl/min.) and to minimise the extra column volume (see schematic diagram in FIG. 7). Whilst the detector was the same as that used for the operation of the 2.1- and 4.6 mm I.D. columns (either a Spectra-Physics Spectra Focus Detector System, (P/N SF102–0122) or an Applied Biosystems Model 120A detector) and 4.5 µl standard flow cell in both of these detectors was replaced by a longitudinal 0.075-mm I.D. fused-silica capillary flow cell (LC Packings, Amsterdam, The Netherlands). The pathlength of this "U-shaped" axial-beam capillary flow cell is 6-mm and the illuminated volume, 26.5 nl.

The accuracy of the flow rate, under gradient elusion conditions, over six consecutive chromatograph runs (calculated from the variance in retention time for lysozyme) was ±0.26%. For protein and peptide separations, extended capillary column usage (e.g., 20–30 consecutive chromatographic runs) often resulted in a 25-percent reduction in the flow rate (i.e., from 4 µl/min. to 3 µl/min.). This was due, presumably, to "dirty" samples which caused partial column/frit blockage and, in the first instance, could be readily corrected by increasing the total flow rate of the liquid chromatograph (from, for example 200 µl/min. to 266 µl/min.). With extended usage, this problem was corrected by (i) replacing the top column frit (for the commercial glass-linked stainless- steel columns) or (ii) by cutting 2-mm off the top of the column (for the fused-silica tube columns that were packed).

In the case of PTH-amino acid separations, the samples were much "cleaner" and the potential problem of frit-plugging was less pronounced thereby extending the column-life.

Mass Sensitivity Achieved with Capillary Columns:

It is established that to operate microbore columns (1–2 mm I.D.) at linear flow velocities equivalent to those used with larger bore columns (≧4.6-mm I.D.), the flow rate must be decreased in proportion to the square of the reduction in column internal diameter. Provided the microbore columns are packed with similar efficiency to that of larger bore columns, and are not overloaded, their sample peak volumes will be proportionally decreased with compared with those from larger bore columns (Scott and Kucera *J. Chromatog,* 169, (1979); Novotny and Ishii (Editors)).

The advantages of narrow bore and capillary columns with respect to enhanced sensitivity of protein detection and reduced peak volumes are shown in FIG. 8. All columns were packed with the same support (Brownlee RP-300, Applied Biosystems) and operated at equivalent linear flow velocities. A comparison of the 4–6-mm I.D. and 2.1-mm I.D. columns revealed that a 5-fold increase in sensitivity of protein detection was achieved by using the 2.1-mm I.D. column. Since the extra-column volumes and detector cell geometry (Hewlett-Packard Model 1090A diode-array cell, 6-mm pathlength, 4.5 µl volume) were identical for the operation of both the 2.1-, and 4.6-mm I.D. columns, such an increase in mass sensitivity is expected. The small variance in retention times between the two columns is due to the variation in column length and to the precolumn instrumental dead volume (about 300 µl) for the instrument used in this experiment (Hewlett-Packard liquid chromatograph Model 1090A).

When the 0.32-mm I.D. capillary column was compared with 2.1- and 4.6-mm I.D. columns, 25- and 125-fold increases in sensitivity of protein detection were achieved, respectively (FIG. 8). The constant peak bandwidths, as a function of time, for the three columns shown in FIG. 8 indicated that comparable column efficiencies can be achieved with capillary liquid chromatograph compared with conventional liquid chromatograph. Peak recovery volumes for the 0.3-, 2.1- and 4.6-mm I.D. columns were 2.5, 133.5 and 660 µl, respectively.

Linearity of Detector Response:

The linearity of the output response of the Applied Biosystems detector (Model 120A), fitted with a 6-mm longitudinal capillary flow cell, was examined using various concentrations of ribonuclease A. For this experiment, ribonuclease A (2.0 mg/ml) was dissolved in 40% acetonitrile/60% water contained 0.1% (v/v) trifluoroacetic (2.0 mg/ml). This stock solution was serially diluted to the required concentrations and 200 µl aliquots were injected directly into the capillary flow cell and the absorbance at 215 nm was measured. It can be seen in FIG. 9 that the output signal of the detector appears to be linear up to about 0.5 absorbance units; this corresponds to a protein concentration of about 125 µg/ml.

To determine the extent to which the detector deviates from linearity, the data in FIG. 9, up to and including absorbance values for protein concentrations 125 µg/ml, were fitted to the formula $$y=Ac^r$$

reported by Scott (Liquid Chromatography Detectors, part 1, Elsevier, Amsterdam, 1977), where y is the detector response, c is the solute concentration, A is a constant, and r is the response index. For ribonuclease A in FIG. 9, the response index r is 0.86 and the correlation coefficient for the curve was 1.00. Although this value of r indicates that the detector deviates slightly from the true linearity—according to Scott Supra, true linearity can only be assumed for values $0.98 \geq r > 1.02$-calibration curves can still be used with reasonable accuracy.

The linearity of detector response using our packed 0.32-mm I.D. capillary column, operated under gradient conditions at a flow rate of 5 µl/min., was investigated using the liquid chromatograph configuration described for system 1. The linearity of the detector was determined by plotting the peak area (arbitrary units) against the amount (micrograms) of lysozyme injected onto the column. FIG. 10 shows that the dynamic linear range of the 6-mm longitudinal capillary flow cell for lysozyme extends to 2 µg. Representative chromatograms for lysozyme in the range 500–2000 ng are shown in FIG. 10(B–D). For the 6-mm pathway capillary flow cell and the equipment used for generating low solvent delivery rates (3–5 µl/min.) (see System 1 in FIG. 7), it would appear that the lower limits of detectability are 50–100 pg. it is estimated herein that the minimum detectable amount (MDA) of lysozyme at 215 nm, using the capillary liquid chromatograph described, which produces a peak that is double the baseline noise (S/N=2) is ca 50 pg (3.6 fmoles). The MDA for ribonuclease A at 215 nm was estimated to be ca 100 pg (7.3 fmoles).

Resolution of Proteins:

FIG. 11 illustrates the separation efficiency that can be achieved for proteins on a reversed-phase capillary column. This chromatogram was obtained with a 50×0.32 mm I.D. RP-300 column, packed by the inventors (see Example 3). Using gradient elution between 0.1% (v/v) aqueous trifluoroacetic acid and acetonitrile –0.1% (v/v) aqueous trifluoroacetic acid (60:40) at a flow rate of 3.6 µl/min. the resolution of this set of proteins (FIG. 11) is as good as that obtained on microbore and larger bore columns packed with the same support. For the 0.32-mm I.D. columns, proteins were recovered in peak volumes of 2–8 µl, which are small enough to allow efficient interfacing with electrospray mass spectrometry (Shelly et al, Supra; Hunt et al (Editors), Methods in Protein Sequence Analysis, Birkhauser-Verlag, Basal, pp 257–266. 1991).

Load Capacity:

The effect of the mass of lysozyme on peak width for a representative 50 mm×0.32 mm I.D. Brownlee RP-300 column is shown in FIG. 12. For protein loads of 50–500 ng there was very little variation in band width (measured by width at peak half height) or band shape. With protein concentrations in excess of 1 µg the band width increased significantly (FIG. 12) which the band profile became distorted (see FIG. 10D), in a similar manner to that described by Snyder et al, I Chromatog. 444: 303–324 (1988). Thus, it would appear that the optimal working range for a column of this dimension is <1 µg and that beyond this, mass-overload as well as detector saturation (see FIG. 9) conditions are encountered.

Peptide Mapping:

An example of a high-sensitivity peptide map obtained with capillary liquid chromatrography is given in FIG. 13. Recombinant mIL-6 (200 ng) was digested with S.aureus V8 protease and the resultant digest chromatographed on 0.32 mm I.D. capillary columns, packed by us (FIG. 13A) or obtained commercially (LC Packings), FIG. 7B, using a trifluoroacetic/acetonitrile gradient elusion system. An inspection of the chromatograms in FIG. 13 indicates that the chromatographic efficiency of our packed column (panel A) compares favourably with that of a commercial capillary column (panel B) and that both of these, in turn, that of a commercial microbore (2.1-mm I.D.) column (panel C). All three columns were packed with the same support (Brownlee RP-300). The flow rates for the capillary columns (panels A and B) were 3.6 µl/min. while the flow rate for the microbore column (panel C) was 178 µl/min. Average peak volumes of 2–8 µl were obtained for the capillary columns (panels A and B), compared to peak volumes of 100–300 µl for the microbore column (panel C).

The sensitivity of peptide mapping on 0.32 mm I.D. capillary columns, demonstrated in FIG. 13, where 300 ng (~10 pmol) of mIL-6 digest was chromatographed is ideally suited to the peptide mapping of proteins resolved by two-dimensional gel electrophoresis (2-DE). Protein spots from six to eight identical 2-DE gels can be readily visualised by high-resolution dynamic imaging (Ward and Simpson, Peptide Res. 4: 187–193, 1991) and then recovered from the gel by passive elusion. For peptide mapping, protein (1–2 µg) can be recovered from the eluate, free of gel-related contaminants by desalting on either reversed-phase or "inverse-gradient" reversed-phase liquid chromatograph (Simpson et al. Eur. J. Biochem. 165: 21–29, 1987; Simpson and Moritz J. Chromatogr. 476; 345–361, 1989).

Multiple-Wavelength Detection:

A multiple-wavelength photometric absorbance monitor (Spectra-Physics, Spectra Focus) was adapted for use in the capillary liquid chromatography system outlined in FIG. 7. The geometry of this monitor, based on a rapidly moving grating, uses a forward-optics system (Carver et al, Am. Lab. 19: 64–71, 1987).

The inventors were interested in establishing whether this multiple wavelength detector, fitted with a 6mm optical pathlength capillary flow cell, could be useful for monitoring the absorbance of the column eluate at 195 nm rather than at 215-nm. This interest was based on the finding by Rosenheck and Doty Proc. Natl. Acad. Sci. U.S.A. 47: 1775–1785 (1961) that the maximal UV absorption for polypeptides occurs at approximately 195nm. FIG. 14 shows the peptide map for a S.aureus V8 digest of mIL-6. Two observations were made: first, the detector signal for peptides was 2–6 fold higher at 195-nm, compared to 215-nm (in FIG. 14, compare peaks C and D); and second, the noise in the baseline at 195-nm is only twice that observed at 215-nm (see insets E and F in FIG. 14B).

Figure 15A:
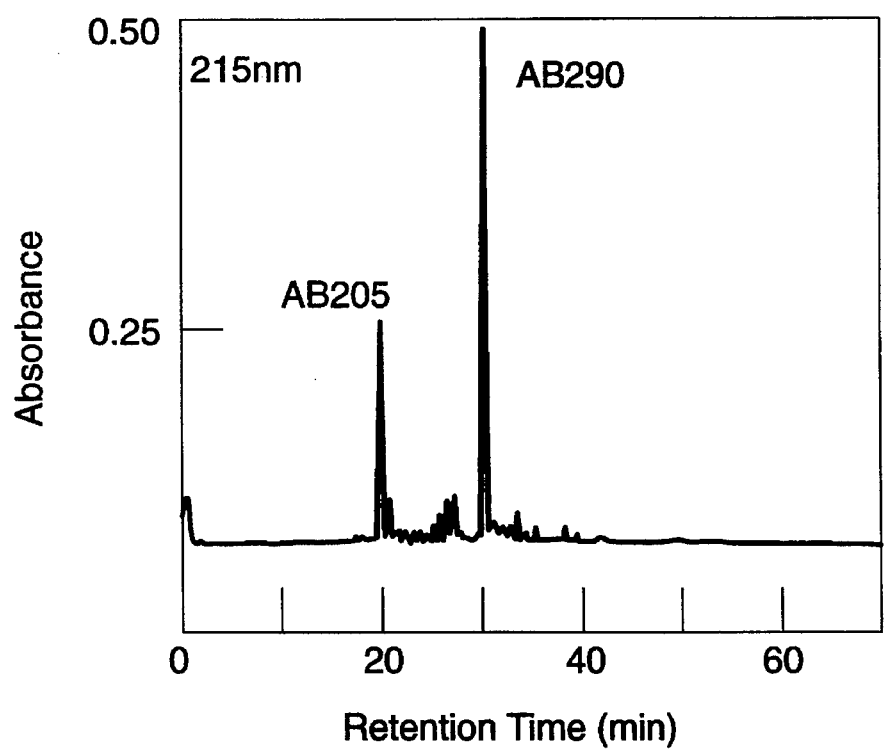
FIG. 15 is a graphical representation showing a spectral analysis of aromatic amino acid-containing synthetic peptides chromatographed by reversed-phase capillary liquid chromatography.
Figure 15B:
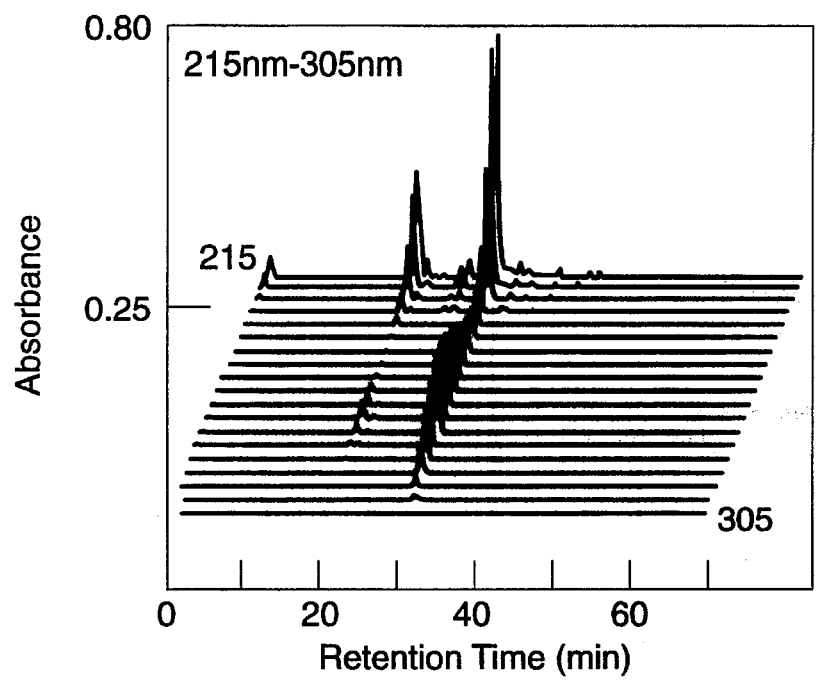

In order to determine whether the multiple-wavelength detector would be useful for identifying aromatic amino acid containing peptides, two synthetic peptides were chromatographed by reversed phase capillary liquid chromatograph (FIG. 15A). Peptide AB205 (SRDMYMESEGGDGY) was a tyrosine-containing 14-residue synthetic peptide and peptide AB290 (DLAWWELR), an 8-residue tryptophan-containing peptide. A multiple signal plot of the data, shown in FIG. 15A, is given in FIG. 15B. An inspection of these spectra reveals major absorption peaks in the range 270 nm–290 nm which are indicative of the aromatic amino acids tyrosine and tryptophan.

Figure 15C:
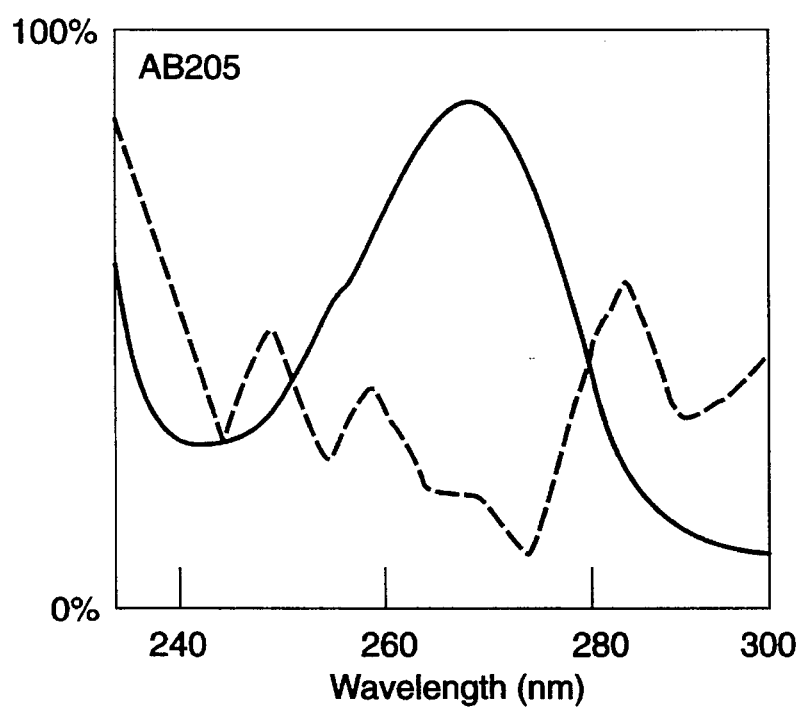
Figure 15D:
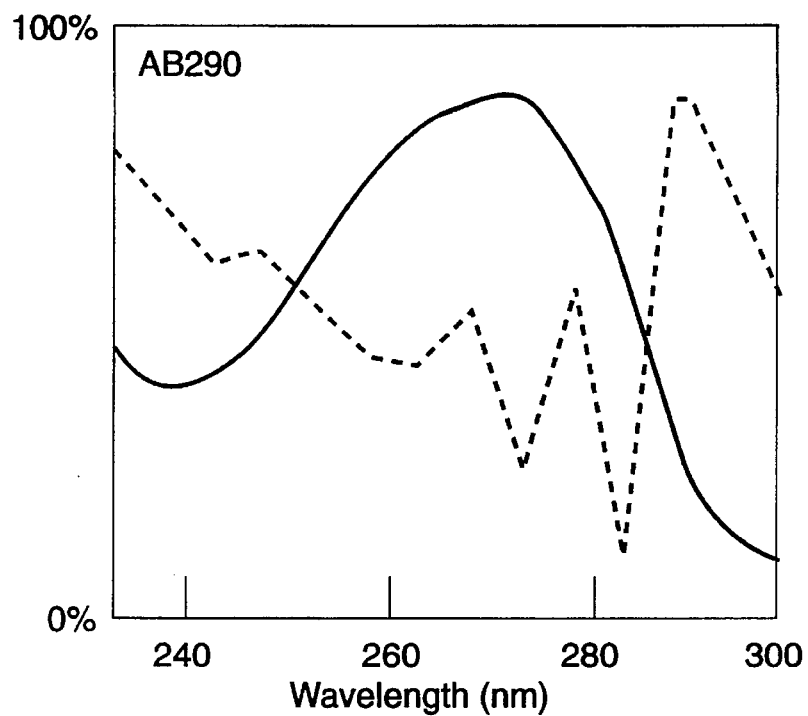

Analysis of the spectra by second-order derivative spectroscopy reveals characteristic minima at 287 nm±5 nm for AB290 and 277 nm±5 nm for peptide AB205 (FIG. 15C and D).

High-Sensitivity Phenylthiohydantoin (PTH)-Amino Acid Anaysis:

This aspect of the present invention defines a method for increasing the sensitivity for detection of PTH-amino acids that relies on the use of reversed-phase capillary liquid chromatography. FIG. 16 illustrates the separation efficiency for PTH-amino acids that can be achieved by capillary liquid chromatograph. The chromatogram was obtained with a 150 mm=0.32 mm I.D. column packed with applied Biosystems PTH-C18 support (LC Packings, Amsterdam). The resolution in FIG. 16 is very similar to that achieved with a commercial 200 mm=2.1 mm I.D. cartridge obtained from Applied Biosystems (Foster City, Calif., U.S.A.); however, the sensitivity of detection of PTH- amino acids using the 0.32 mm I.D. capillary column is, conservatively 25-fold higher (25-femtamoles) than that achievable with the 2.1 mm I.D. column.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

We claim:

1. A method for conducting a chemical reaction, the method comprising: immobilizing a first reactant at an electrode defining a reaction locus; introducing an additional reactant to the reaction locus; electrolytically activating a reaction between the first and additional reactants; and removing remaining additional reactant or a reaction by-product from the reaction locus, wherein said method further comprises resolving, separating, or purifying at least one reactant by using a capillary liquid chromatographic system comprising a capillary column of $\leq 0.50$ mm I.D. packed with bonded-phase particles having from about 200 Å to about 500 Å pore size.

2. A method according to claim 1 wherein the capillary column is $\leq 0.40$ mm I.D.

3. A method according to claim 2 wherein the capillary column is $\leq 0.32$ I.D.

4. A method according to claim 1 wherein the capillary column is slurry-packed with from about 5 μm to about 20 μm diameter $C_8$ bonded-phase particles.

5. A method according to claim 4 wherein the $C_8$ bonded-phase particles are about 7 μm in diameter and have a pore size of approximately 300 Å.

6. Apparatus for conducting a chemical reaction, the apparatus comprising an electrode disposed at a reaction locus: means to immobilize a first reactant at the reaction locus; means to introduce an additional reactant to the reaction locus; means to energize the electrode to thereby electrolytically activate a reaction between the first and additional reactants or to electrophoretically attract the additional reactant to the reaction locus; means to remove from the reaction locus, remaining additional reactant or a reaction by-product of the reaction, wherein said apparatus further comprises a capillary liquid chromatographic system to resolve, separate, or purify the reactant or reactant by-product comprising a capillary column of $\leq 0.50$ mm I.D. packed with bonded-phase particles having from about 200 Å to about 500 Å pore size.

7. Apparatus according to claim 6 wherein the capillary column is $\leq 0.40$ mm I.D.

8. Apparatus according to claim 7 wherein the capillary column is $\leq 0.32$ I.D.

9. Apparatus according to claim 6 wherein the capillary column is slurry-packed with from about 5 μm to about 20 μm diameter $C_8$ bonded-phase particles.

10. Apparatus according to claim 9 wherein the $C_8$ bonded-phase particles are about 7 μm in diameter and have a pore size of approximately 300 Å.

* * * * *